US005501959A

United States Patent [19]
Lancaster et al.

[11] Patent Number: 5,501,959
[45] Date of Patent: Mar. 26, 1996

[54] ANTIBIOTIC AND CYTOTOXIC DRUG SUSCEPTIBILITY ASSAYS USING RESAZURIN AND POISING AGENTS

[75] Inventors: Michael V. Lancaster; Rebecca D. Fields, both of Woodland, Calif.

[73] Assignee: Alamar Biosciences Laboratory, Inc., Chicago, Ill.

[21] Appl. No.: 396,362

[22] Filed: Feb. 28, 1995

Related U.S. Application Data

[63] Continuation of Ser. No. 312,485, Sep. 26, 1994, abandoned, which is a continuation of Ser. No. 150,564, Nov. 10, 1993, abandoned, which is a continuation of Ser. No. 856,109, Mar. 23, 1992, abandoned, which is a continuation-in-part of Ser. No. 298,599, Jan. 17, 1989, abandoned.

[51] Int. Cl.[6] .............................. C12Q 1/18; C12Q 1/02; C12N 5/02; C12N 1/02
[52] U.S. Cl. ........................... 435/32; 435/29; 435/240.2; 435/243
[58] Field of Search ........................... 435/29, 32, 240.2, 435/243

[56] References Cited

U.S. PATENT DOCUMENTS

| | | | |
|---|---|---|---|
| 3,107,204 | 10/1963 | Brown | 435/32 |
| 3,963,580 | 6/1976 | Vendamuthu | 435/885 |
| 4,385,115 | 5/1983 | de Zabala et al. | 435/33 |

FOREIGN PATENT DOCUMENTS

| | | |
|---|---|---|
| 1112140 | 11/1981 | Canada . |
| 42-25409 | 12/1967 | Japan . |
| 43-19817 | 8/1968 | Japan . |
| 2-12056 | 1/1990 | Japan . |
| 2-211899 | 8/1990 | Japan . |

OTHER PUBLICATIONS

Baker et al. (1980) Microbiology 26:248–253.
Kanazawa et al. (1966) J. Antibiotics 19:229–233.
Brown et al. (1961) J. Clin. Path. 35:10–13.
Cohen, Barnett et al., "Intracellular Oxidation–Reduction Studies", J. Gen. Physiol., 11:585 (1928).
Coulter, Calvin B., "Oxidation–Reduction Equilibria in Biological Systems", 139–45 (Apr. 1928).
Dubos, Rene, "Observations on the Oxidation–Reduction Properties of Sterile . . . ", 507–523 (Nov. 1928).
Dubos, Rene, "The Relation of the Bacteriostatic Action of Certain Dyes . . . ", 575–592 (Nov. 1928).
Dubos, Rene, "The Initiation of Growth of Certain Facultative Anaerobes as Related . . . ", 559–73 (Nov. 1928).
Fildes, Paul, "Tetanus.—VIII. The Positive Limit of Oxidation–Reduction . . . ", 151–75, (Jan. 10, 1929).
Fildes, Paul, "Tetanus.—IX. The Oxidation–Reduction Potential of The Subcutaneous . . . ", 197–204, (Mar. 25, 1929).
Knight, Bert, "CXXII. Oxidation–Reduction Studies in Relation to Bacterial Growth", 1066–74 (Jun. 30, 1930).
Knight, Bert, "CXXIII. Oxidation–Reduction Studies in Relation to Bacterial Growth", 1075–1079 (Jun. 30, 1930).
Cohen, Barnett, "The Bacterial Culture as an Electrical Half–Cell", J. Bact. 21:19 (1931).
Cohen, Barnett, "Reactions of Oxidation–Reduction Indicators in Biological . . . ", Cold Spring Harbor Symp. Quart Biol. 1:214 (33).
Michaelis, Leonor, "Reversible Two–Step Oxidation", Cold Spring Harbor Symp. Quart Biol. 1:224 (1933).
Clifton, C. E. et al. " Oxidation–Reduction Potentials and Ferri–Cyanide Reducing . . . ", J. Bact. 28:541 (1934).
Clifton, C. E. et al., "Oxidation–Reduction Potentials and Ferricyanide Reducing . . . ", J. Bact. 28:561 (1934).
Clark, W. Mansfield, "The Potential Energies of Oxidation–Reduction Systems . . . ", Medicine, 13:207 (1934).
Clifton, C. E., "A Comparison of the Metabolic Activities of Aerobacter Aerogenes, . . . ", J. Bact. 33:145 (1937).
Hanke, Martin E., "An Electrolytic Method for Controlling Oxidation–Reduction", 183–200 (Mar. 12, 1943).
Hewitt, L. F., "Oxidation–Reduction Potentials in Bacteriology and Biochemistry", 95–136 (1950).
Rajam, P. C., "A Rapid Test for Screening the Sensitivity of Staphylococci . . . ", AMJ Clin. Path. 23:1168–1172 (1953).
Sorensen, Royal H., "Rapid Antibiotic Sensitivity Test Using a Redox Indicator", 144–150 (1959).
Dobson, A. et al., "A Method for the Control of Eh and pH during Bacterial Growth", J. Gen. Microbiol. 35:169–174 (1964).
Lorian, Victor, "Antibiotics and Chemotherapeutic Agents in Clinical and Laboratory . . . ", 73–143 (1966).
Jacob, H. E., "Redox Potential", In J. R. Norris and D. W. Ribbons ed. Method of Microbiol., 2:92–123, N.Y., (1970).
Tabatabai, L. B., "Oxidation–Reduction Potential and Growth of Clostridium perfringens . . . ", App. Microb., 441–446 (Sep. 1970).
Boyle, V. James, "Rapid, Modified Kirby–Bauer Susceptibility Test with Single . . . ", Antimicrobial Ag., pp. 418–424, (Mar. 1973).
Walden, William C., "Differential Effects of Oxygen and Oxidation–Reduction . . . ", Applied Microb. 781–785, Nov. 1975.

(List continued on next page.)

Primary Examiner—David M. Naff
Assistant Examiner—L. Blaine Lankford
Attorney, Agent, or Firm—Townsend and Townsend and Crew

[57] ABSTRACT

Growth inhibition assays for both microorganisms and mammalian cells are performed by incubating the microorganisms or cells in a growth medium in the presence of resazurin and a suspected growth inhibiting agent. By observing a color change accompanied by the reduction of resazurin to resorfurin, continued cell viability can be determined. The present invention reduces system errors by inhibiting the autoreduction of resazurin by the growth media by incorporating suitable redox stabilizing agents in the medium. In a preferred embodiment the poising agent is potassium ferrocyanide, ferric salt or ferricinium and the medium is maintained at a potential from about +0.3 volts to about +0.45 volts. A second poising agent can be used to inhibit the reduction of resorfin to dihydroresorfin. Preferred second poising agents are methylene blue, toluidine blue, azure I and gallocyanide in amounts to maintain the potential of the growth medium above −0.1 volts.

23 Claims, 10 Drawing Sheets

OTHER PUBLICATIONS

Onderdonk, A. B. et al., "Effect of Dissolved Oxygen and Eh on Bacteroides fragilis . . . ", App. & Env. Micro., Feb. 1976, 168–72.

Bartlett, R. C., "Acceleration of Tetrazolium Reduction by Bacteria", J. of Clin. Micro. Mar. 1976, 327–329.

Bartlett, R. C., "Rapid Antimicrobial Susceptibility Test Using Tetrazolium Reduction", Anti. Ag. & Chemo., 769–774 (Jun. 1979).

Lancaster et al., (1990) Abstracts of the Annual Meeting p. 386, #C–255.

Kelley et al. (1987) Abstracts of the Annual Meeting p. 332, 190 C–57.

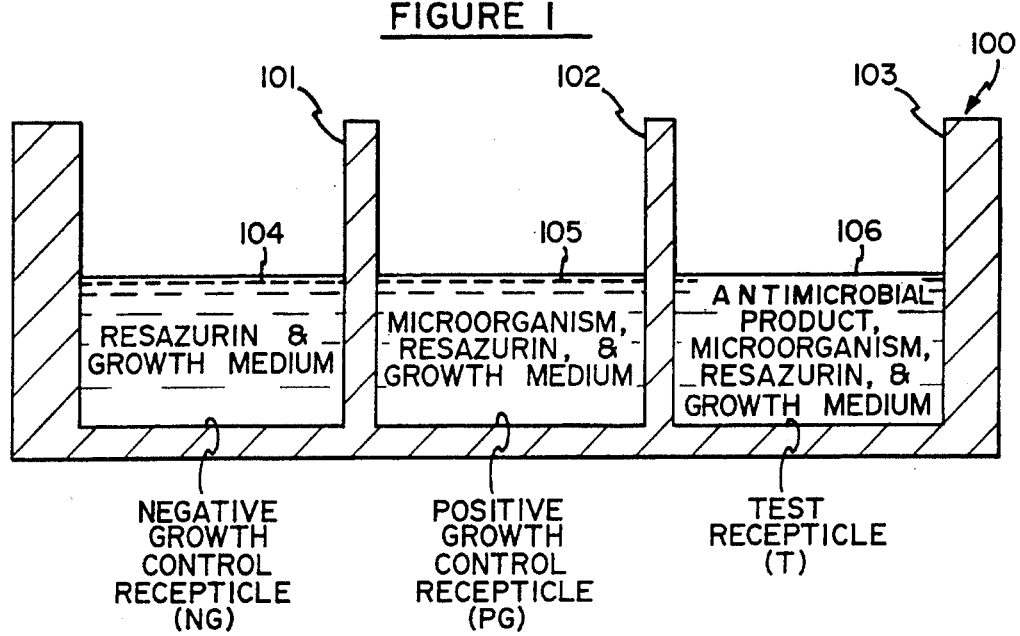
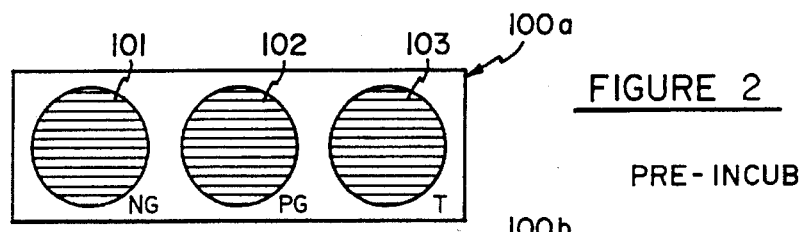
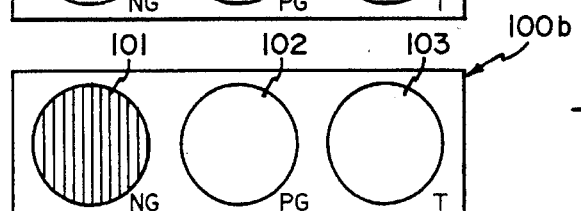
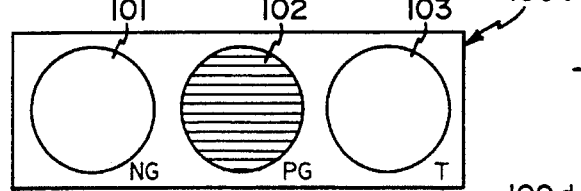
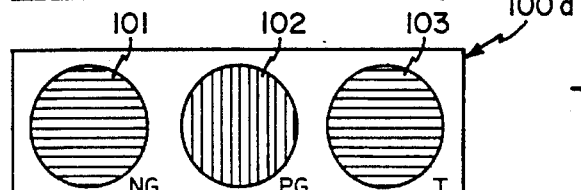
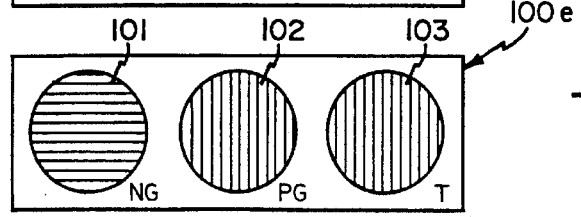

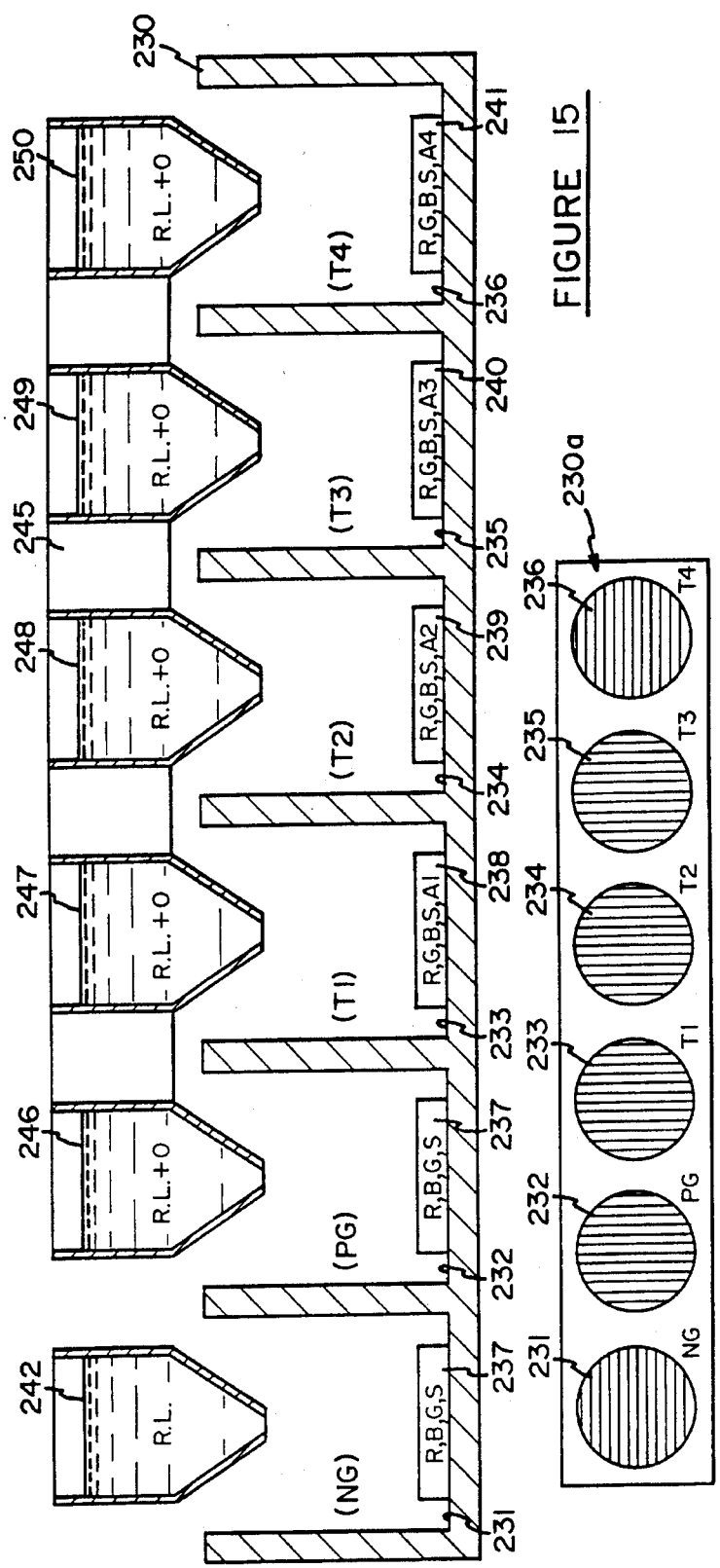
FIGURE 15
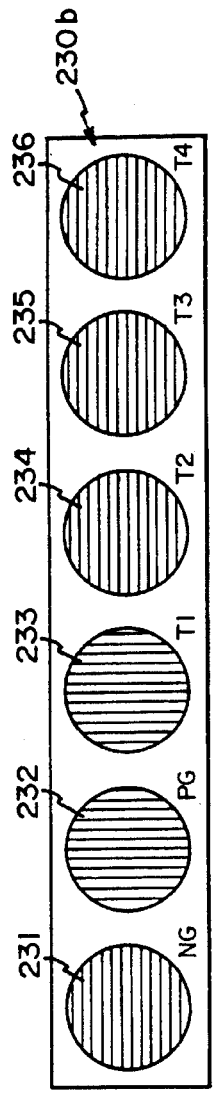
FIGURE 16
FIGURE 17

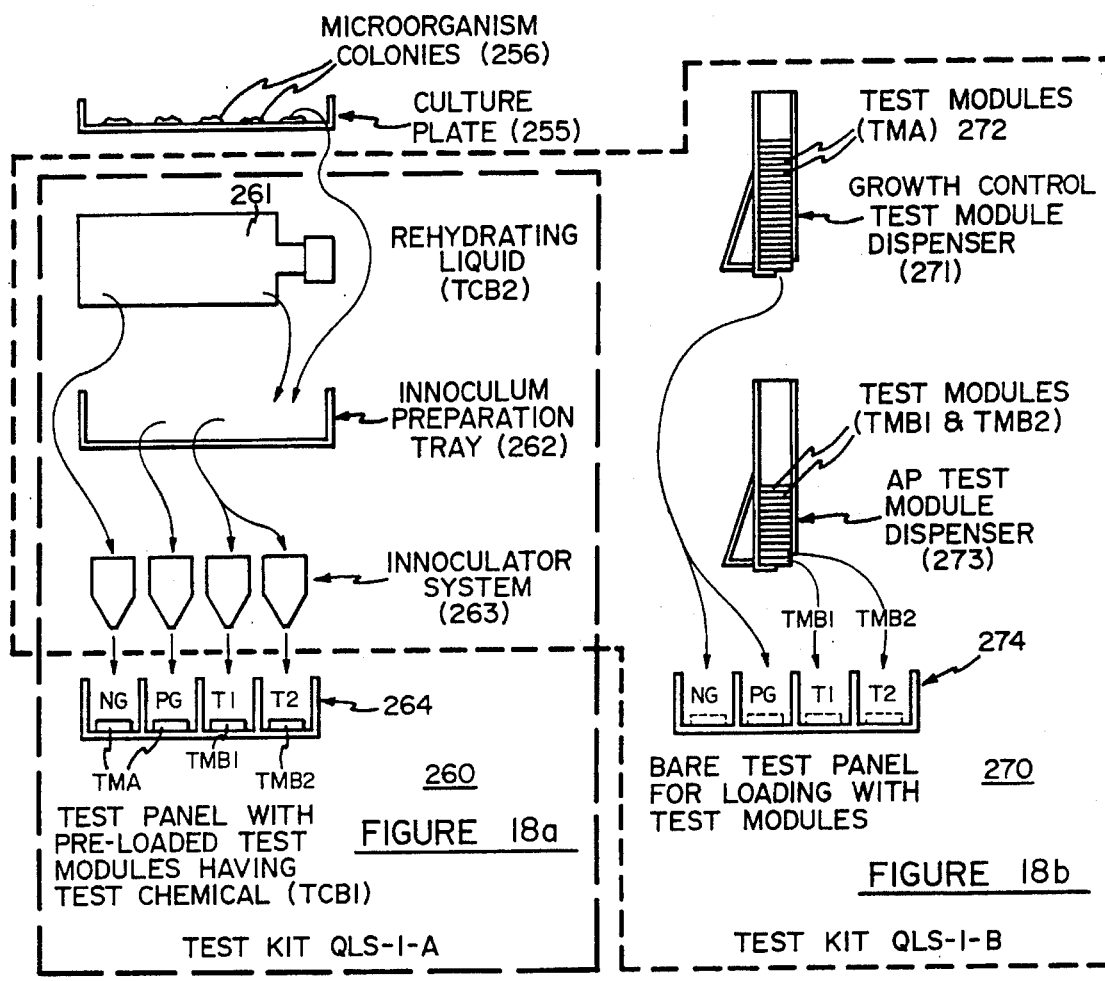
QUALITATIVE SUSCEPTIBILITY TEST KITS
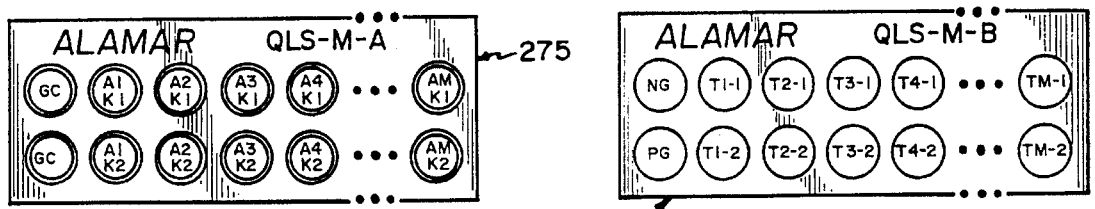
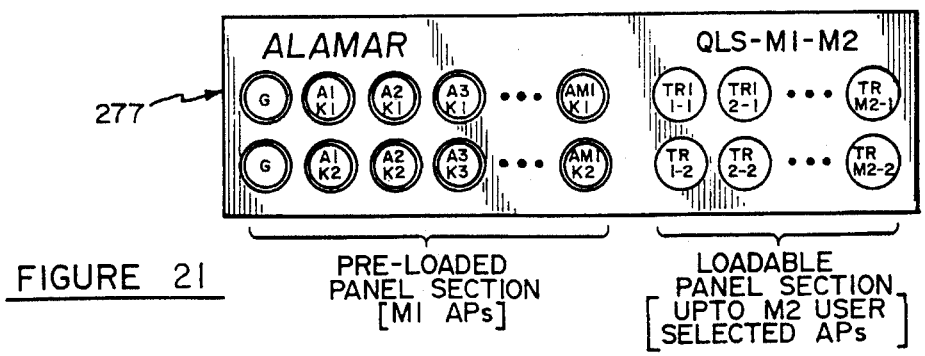

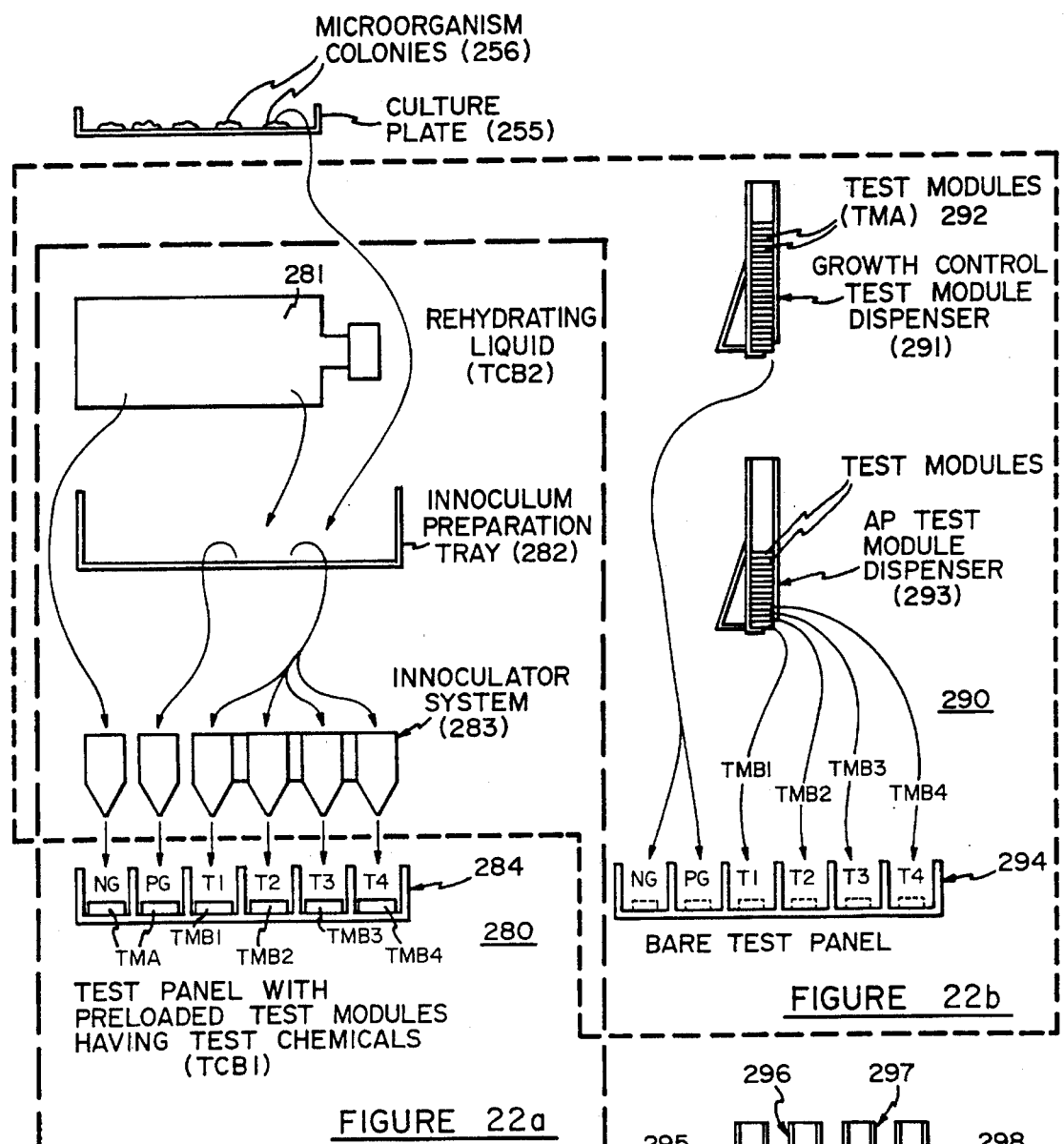
FIGURE 22a
FIGURE 22b
QUANTITATIVE SUSCEPTIBILITY TEST KITS
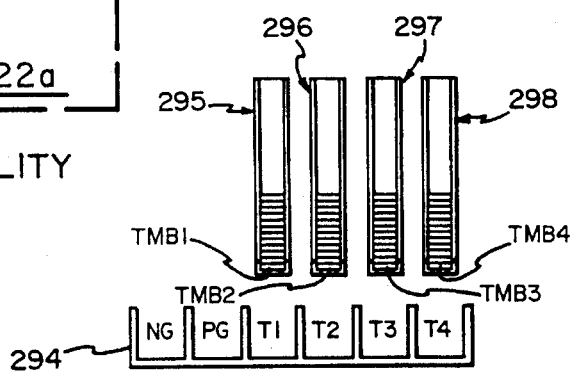
FIGURE 23

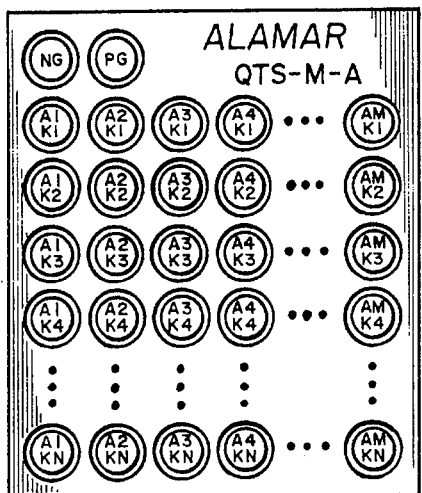
FIGURE 24
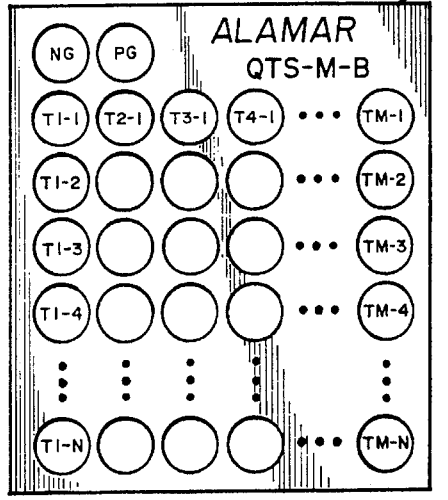
FIGURE 25
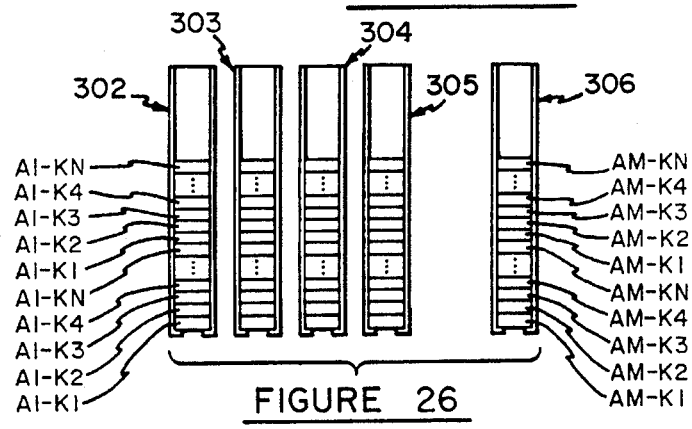
FIGURE 26
FIGURE 27
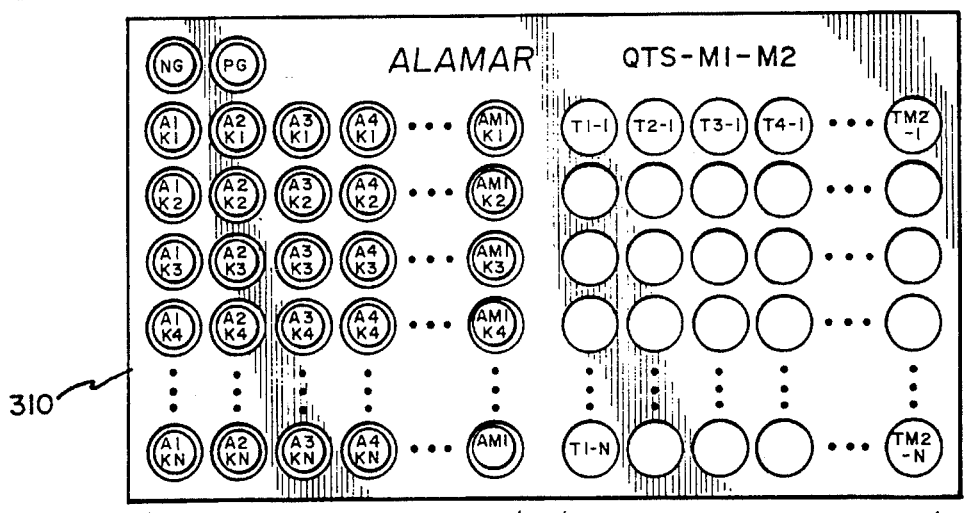

E. COLI GROWTH CURVES MEASURED BY
CFU, TURBIDITY, FLUOROGENICS, REDOX

GROWTH RESPONSES OF SELECTED SPECIES
MEASURED BY REDOX RESPONSE

ANTIBIOTIC AND CYTOTOXIC DRUG SUSCEPTIBILITY ASSAYS USING RESAZURIN AND POISING AGENTS

This is a continuation of application Ser. No. 08/312,485, filed Sep. 26, 1994, which was a CON of U.S. Ser. No. 08/150,564; filed Nov. 10, 1993, which was a CON of U.S. Ser. No. 07/856,109; filed Mar. 23, 1992, which was a CIP of U.S. Ser. No. 07/298,599; filed Jan. 17, 1989, all abandoned.

BACKGROUND OF THE INVENTION

1. Field of the Invention

This invention relates generally to apparatus and methods for testing the susceptibility of microorganisms and mammalian cells to growth inhibition by antimicrobial and cytotoxic products. This invention further relates to both qualitative and quantitative susceptibility testing.

Microorganism and cellular specimens to be tested may be supplied to a laboratory from a number of sources. The specimens may be collected by doctors in their offices and sent to a central testing laboratory or the specimens may be collected from patients in hospital with which the laboratory is associated. The microorganism specimens may come from various parts of the body, for example, from cerebral spinal fluid, an abscess, an infected wound, genital infections, etc. The cellular specimens will usually be from tumor biopsies specimens. The collected specimens are cultured on a suitable media in accordance with normal laboratory practice. From the bacterial colonies and cellular clones on the primary culture plate, an inoculum is prepared in accordance with an established procedure which produces a bacterial or cellular suspension of a prearranged concentration. Further processing of the suspension depends on the apparatus and method to be used for susceptibility testing.

The purpose of bacterial susceptibility testing is to provide information to the referring physician on the probable success of the antibiotic drug therapy that has already been initiated. The physician will generally prescribe an antimicrobial product, commonly called an antibiotic drug, to be administered before the test results are known, but it is often important for the physician to learn whether that antimicrobial product and/or the concentration given will successfully kill the microorganism that is causing the infection. After the test results are in, the physician can change the drug therapy if the test results show that there is a reason to do so.

The purpose of cellular cytotoxicity testing is usually to determine the susceptibility of the tumor cells to particular chemotherapeutic drugs.

The term qualitative susceptibility testing refers to testing apparatus and methods which produce test results that generally indicate whether an organism or cellular specimen is sensitive or resistant to a particular antibiotic or cytotoxic product. Depending on the method involved only one or two concentrations of antimicrobial product are usually utilized. The degree of sensitivity or resistance is not reported in qualitative susceptibility testing.

The term quantitative susceptibility testing refers to testing apparatus and methods which produce test results that provide data on the concentration of the antimicrobial or cytotoxic product that will be sufficient to inhibit growth of the microorganism or tumor cells. Typically, for microorganism specimens, six or more different dilutions of the antimicrobial product are utilized covering the therapeutic range of concentrations of the antimicrobial product. The term Minimum Inhibitory Concentration (MIC) is often used to refer to the result provided by quantitative susceptibility testing of microorganism and is defined as the minimum concentration of the antimicrobial product which will produce inhibition of the growth of the microorganism.

The term antimicrobial product will be used herein to designate a product that contains one or more antimicrobial agents (i.e. individual antibiotics) in prearranged concentrations and is thus a general designation for a single antibiotic drug or a broad spectrum formulation that contains more than one antibiotic agent. The term cytotoxic product will be used herein to designate a product that contains one or more drugs which are capable of inhibiting the growth of human and/or other mammalian tumor cells.

The use of oxidation-reduction (redox) indicators for antimicrobial susceptibility testing has been proposed but has not yet found widespread use. In theory, microbial growth can be detected by incubation with a redox indicator which changes color when reduced from an oxidized state to a reduced state by the metabolic processes of the microorganism. Particular indicators which have been proposed for such testing include tetrazolium and resazurin.

Of particular interest to the present invention is the use of resazurin as a redox indicator for detecting microbial growth in susceptibility tests. Test protocols which have been proposed include incubation of sample containing a test organism in a growth medium containing resazurin and an antimicrobial agent. Growth inhibition by the antimicrobial agent can then be detected by visually comparing the color of the growth medium with the color of the medium of a test sample containing growth medium but no antimicrobial agent.

While such test protocols utilizing resazurin promise convenience, accuracy, and use with many types of organisms, they have suffered from certain limitations which have prevented their widespread use. In particular, resazurin is subject to autoreduction in most growth media, i.e. the resazurin will be reduced and change color even when microbial growth is absent. Thus, the use of negative test controls is problematic, particularly over extended time protocols such as overnight tests. Many non-stabilized media, such as brain heart infusion broth, cause reduction of the resazurin over time and are generally unsuitable for performing protocols over periods approaching 24 hours.

Autoreduction of the resazurin is less of a problem with relatively short test protocols, i.e. several or fewer hours, but such short protocols are less useful in detecting growth of weakly growing microorganisms. Indeed, many weakly growing organisms require extended incubation protocols approaching 24 hours, which protocols are rendered difficult or impossible because of the media instability problems just discussed.

Thus, it would be particularly desirable to provide improved media and methods which employ resazurin as a microbial growth indicator, where the media and methods are particularly stable and permit extended incubation protocols without significant autoreduction.

2. Description of the Background Art

The use of absorbent pads impregnated with resazurin and antibiotics for antimicrobial susceptibility testing is described in Baker et al. (1980) Microbiol. 26:248–253 and Canadian Patent 1,112,140. Bacterial isolates are applied to the pad in a brain heart infusion broth. The protocols described, however, are generally not suitable for determining minimum inhibitory concentrations (MIC). Kanazawa et. al. (1966) *J. Antibiotics* 19:229–233 also describes the use of absorbent pads impregnated with resazurin and antimicrobials for susceptibility testing. Brown et al. (1961) *J. Clin. Path.* 5:10–13 and U.S. Pat. No. 3,107,204 describe the use of absorbent pads impregnated with another redox indicator (tetrazolium) and antimicrobials in susceptibility testing. Japanese patent publication 2-211899 teaches that resazurin susceptibility tests may run in Mueller-Hinton broth and may be detected based on fluorescence. Japanese patent publications 2-12056, 43-19817, and 42-25409 are also relevant to susceptibility assays employing resazurin as a redox indicator.

The full disclosures of each of these references are incorporated herein by reference.

SUMMARY OF THE INVENTION

According to the present invention, methods and compositions are provided for performing growth inhibition assays. The assays are useful not only with microorganisms, such as bacterial, yeast, fungi, and protozoa, but also with cultured mammalian cells. In the case of microorganisms, the assays will be particularly useful for antimicrobial susceptibility testing, i.e. determining which antimicrobial agents are effective against a tested strain of microorganism and are thus useful for therapeutic purposes. In the case of cultured mammalian cells, the assays will be particularly useful for screening cytotoxic drugs capable of inhibiting the growth of neoplastic cells, more particularly for screening drugs useful in the treatment of cancer and other neoplastic diseases. For convenience, microorganisms and mammalian cells will be referred to generically hereinafter as "cultured cells."

The method of the present invention relies on culturing the cells in a growth medium in the presence of resazurin and a growth inhibiting substance, such as an antimicrobial agent or a cytotoxic drug. Most commonly, known antimicrobial agents and cytotoxic drugs will be tested for the purpose of determining which chemotherapeutic modalities would be most effective against the infection or cancer. The present invention, however, could also be utilized with unknown or suspected antimicrobial agents and drugs for the purposes of determining potential activity, e.g., screening relatively uncharacterized substances for anti-microbial activity as part of drug screening or other activities.

The improvement of the present invention relates to certain measures taken for stabilizing the resazurin in the growth medium to inhibit autoreduction, to resorufin, a red-colored product which is the desired end point when microbial or cellular growth is present. As described above, the resazurin will autoreduce in most or all growth media, where such autoreduction can cause a false change in color or fluorescence, both in the control and test samples. The inventors herein have found that the incorporation of certain oxidation-reduction (redox) stabilizers, also referred to as poising agents, can substantially prevent autoreduction of the resazurin for extended time periods, usually for at least 24 hours or longer. Surprisingly, it has been found that the redox stabilizers can be added to the growth medium without substantially affecting the desired reduction which takes place as a result of cellular metabolism, even when the microorganisms or mammalian cells provide only weak metabolic reduction. Additionally, the stabilization measures have been found to inhibit autoreduction in microbial cultures for periods of 24 hours and longer and in mammalian cell culture for periods of several days and longer. Previous resazurin formulations would have been unsuitable for mammalian culture which generally require longer culture periods.

Preferably, the redox stabilizers are salts selected to maintain the redox potential of the growth medium in the range from about +0.3 volts to +0.45 volts in the absence of microorganism or cellular growth. Particularly suitable redox salts include ferricyanide, ferricinium, ferric sulphate, and others from the electrochemical series which have correct potentials, are non-toxic, and are soluble at needed concentrations and pH. Even more preferred are the addition of coupled pairs of reduced and oxidized salts, such as ferricyanide/ferrocyanide, ferricinium/ferrocene, ferric/ferrous salts, and others which meet the above criteria.

According to an even more preferred aspect of the present invention, methylene blue or other suitable second poising agent will be added to the growth medium both as a redox stabilizer and as a redox indicator. It has been found that methylene blue stabilizes the redox potential of the growth medium in the range from about −0.1 volts to +0.1 volts after the resazurin has been reduced to resorufin. Such stabilization prevents the further reduction of resorufin to dihydroresorufin, a non-colored, non-fluorescent product which results in loss of the desired end point. Methylene blue also enhances the deep blue color of the oxidized resazurin prior to reduction to resorufin.

In an exemplary embodiment, the resazurin, poising agent(s), methylene blue, and growth inhibiting substance will be impregnated into an absorptive pad, usually a paper disk, and disposed on a test card. The test card will carry at least one "positive" control well (i.e., without growth inhibiting substance) and at least one, and usually a plurality of test wells incorporating different antibiotics or cytotoxic agents, the same antibiotic or cytotoxic agent at different concentrations, or combinations thereof. The test is then run by applying the growth medium to the absorptive pad, usually in combination with the cultured cells. At least one of the test wells will be inoculated without microorganisms or cells to produce a negative control well. Test results will be read after sufficient time has elapsed to produce a color change in the presence of cellular growth. While the present invention can provide for rapid growth protocols, it will be particularly suitable for extended growth protocols without substantial autoreduction of the resazurin. Test kits will employ the test cards, growth medium, instructions, and other components necessary for performing the test.

BRIEF DESCRIPTION OF THE DRAWINGS

FIG. 1 illustrates the general method and apparatus for determining the susceptibility of a microorganism to growth inhibition by an antimicrobial product in accordance with this invention.

FIGS. 3–5 illustrate a visible light reading protocol in accordance with this invention.

FIG. 15 illustrates use of the method and apparatus of this invention in a quantitative susceptibility test panel.

FIGS. 16 and 17 are illustrative examples of a visible light reading protocol for the quantitative susceptibility test panel of FIG. 17.

FIGS. 18A and 18B illustrate components of alternative embodiments of qualitative susceptibility test kits in accordance with this invention.

FIG. 19 illustrates a qualitative susceptibility test panel in accordance with this invention with preloaded test modules for multiple antimicrobial products.

FIG. 20 illustrates a qualitative susceptibility test panel in accordance with this invention with test wells loadable with user selected test modules for multiple antimicrobial products.

FIG. 21 illustrates a qualitative susceptibility test panel in accordance with this invention with both preloaded and bare test wells for multiple antimicrobial products.

FIGS. 22A and 22B illustrate components of alternative embodiments of quantitative susceptibility test kits in accordance with this invention.

FIG. 23 illustrates an alternative set of test kit components for loading test modules into test wells of a bare test panel for quantitative susceptibility testing.

FIG. 24 illustrates a quantitative susceptibility test panel in accordance with this invention having preloaded test modules for multiple antimicrobial products.

FIG. 25 illustrates a quantitative susceptibility test panel in accordance with this invention having bare test wells for loading with user selected test modules for multiple antimicrobial products.

FIG. 26 illustrates test kit components for loading test modules for multiple antimicrobial products into bare test wells of a test panel in accordance with this invention.

FIG. 27 illustrates a quantitative susceptibility test panel in accordance with this invention having a section of preloaded test modules for multiple preselected antimicrobial products and a section of bare test wells for loading of test modules for multiple user selected antimicrobial products.

DESCRIPTION OF THE PREFERRED EMBODIMENT

The Basic Methodology (FIGS. 1–7)

Figure 7:
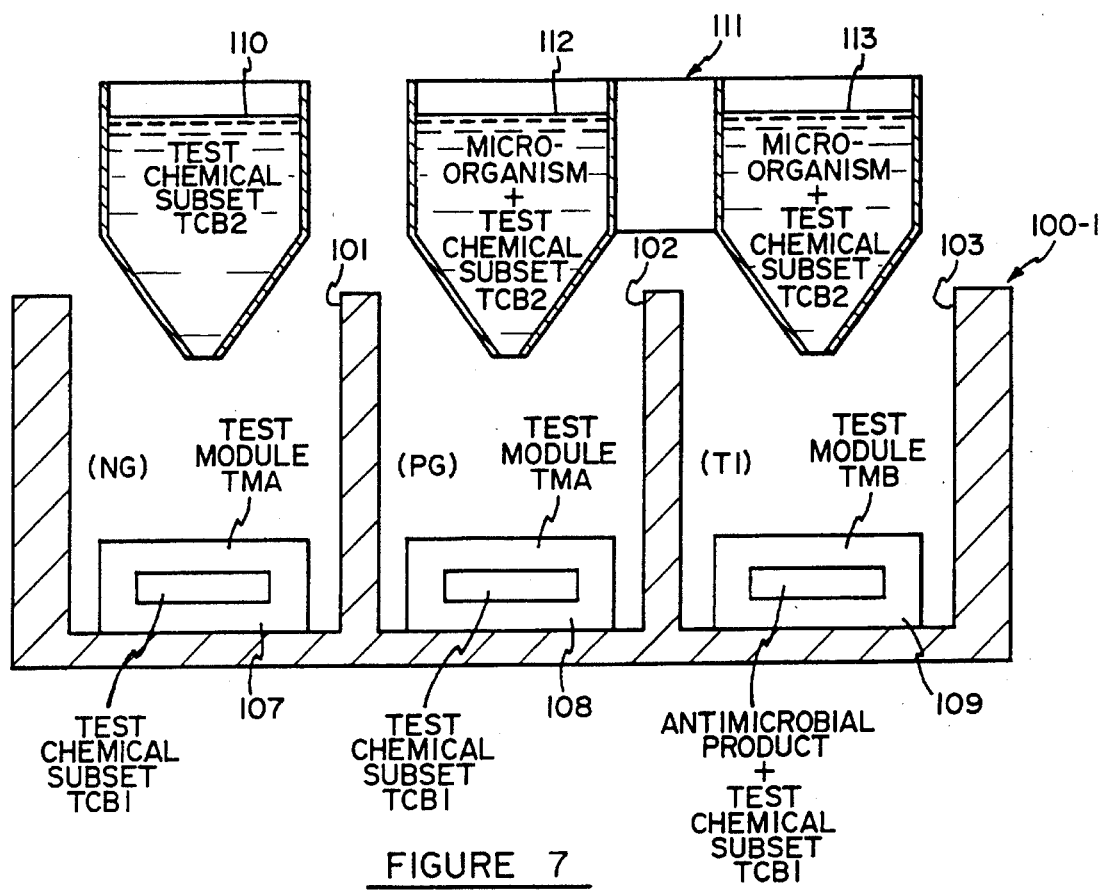
FIGS. 7–10 illustrate various alternative embodiments of method and apparatus for determining the susceptibility of a microorganism to growth inhibition by an antimicrobial product in accordance with this invention.

The basic method of this invention involves testing the susceptibility of a microorganism or cellular sample to growth inhibition by a preselected concentration of an antimicrobial or cytotoxic product utilizing a test panel 100 with a negative growth control well or receptacle 101, a positive growth control well or receptacle 102, and a test well or test receptacle 103. The term "well" or "receptacle" will be used interchangeably in this description with the understanding that the term "receptacle" is general to any appropriate structure that for holding the test chemicals. The method is not dependent upon use of a multiwell panel, and separate individual receptacles could be used. The panel approach is preferred for simplicity of handling in and out of the incubator and for other reasons that are well known to persons in this art. The general steps of the method will now be described.

A prearranged concentration of a growth medium for microorganisms or mammalian cells is disposed in the two growth control receptacles 101 and 102 and a prearranged concentration of resazurin is also disposed in both growth control receptacles. The growth medium is selected to minimize autoreduction of the resazurin (i.e. is non-reducing), with Mueller-Hinton broth being preferred for microbial culture. Other suitable media for microbial culture include Trypticase Soy Broth. Non-reducing growth media for mammalian cell culture include RPMI 1640, RPMI 1640 supplemented with fetal calf serum (FCS, 10%), Hank's Modified Eagle Medium, and Dulbecco's Modified Eagle Medium.

The concentration of the selected growth medium may be in the standard range of concentrations currently used in the susceptibility testing industry. The concentration of resazurin used is in a predetermined range characterized by low toxicity to microorganisms (or mammalian cells) and substantial sensitivity to reduction to resorufin by the metabolic products of microorganism cellular growth.

A prearranged concentration of the microorganisms or mammalian cells to be tested is disposed in the positive growth control well 102. Thus, as shown in FIG. 1, the negative growth control well 102 contains growth medium and resazurin while the positive growth control well contains growth medium, resazurin and the microorganisms or cells.

In the test well 103 the following test chemicals are disposed: the antimicrobial or cytotoxic product in the preselected concentration, the same prearranged concentration of growth medium as in the two growth control wells, the same concentration of resazurin and the same concentration of the microorganism or cells as in the positive growth control well.

The growth medium in all three test wells will further comprise component(s) which stabilize the oxidation-reduction equilibrium of the growth medium to inhibit auto reduction of the resazurin over time. It has been found by the inventors herein that the use of resazurin as a metabolic growth indicator is limited since it is subject to an unstable end point after extended time periods, i.e., that autoreduction of the resazurin (even in the absence of microbial or mammalian cellular growth) will cause the medium to change color from blue to red. Thus, previous resazurin susceptibility tests have been generally unsuitable for overnight and other extended-period testing protocols. The tests of the present invention overcome such limitations by inhibiting autoreduction using measures as will be described.

As a first measure to inhibit autoreduction of the resazurin, a pair of coupled poising agents will be added to the growth medium to stabilize the oxidation-reduction potential within the range where the resazurin is oxidized, i.e. blue. Poising agents will be selected to maintain the oxidation-reduction potential in the range from about +0.3 volts to +0.45 volts, preferably in the range from about +0.325 volts to +0.375 volts. Suitable poising pairs including ferricyanide/ferrocyanide, ferrous/ferric, and the like.

Use of ferricyanide/ferrocyanide as the coupled poising agents is preferred. The concentrations and ratios of the ferricyanide and ferrocyanide in the growth media will affect the stability of the resazurin and will be selected to control the autoreduction effect. Concentration affects the capacity to hold at a predetermined desired redox potential, thereby affecting the amount of activity either from autoreduction or metabolic activity required to begin reduction of resazurin to resofurin. Excess concentration of the poising pair will inhibit activity and decrease sensitivity of the system.

The ferricyanide/ferrocyanide ratio affects the actual redox potential value and controls the beginning potential. Too high beginning potential creates a large oxidation state to overcome, delaying or inhibiting desired metabolic reduction. Too low contributes to drift by allowing small reduction to be detected.

The preferred concentration is 0.0001M, with a range of 0.00005M to 0.001M total concentration of both components being useful. The preferred ferricyanide/ferrocyanide ratio is 1:1 with ratios of 1:4 to 4:1 of ferricyanide/ferrocyanide being acceptable.

In addition to the coupled poising agents, the growth media of the present invention will preferably further include a second poising agent, which is itself a reversible oxidation-reduction indicator. It has been found that methylene blue acts to stabilize the oxidation-reduction potential of the growth medium and inhibit resazurin (i.e., resorufin) to dihydroresorufin, which is a generally uncolored product. Other suitable second poising agents include toluidine blue, azure I, and gallocyanine. Additionally, the methylene blue enhances the intensity of the blue when the system is in its oxidized state, i.e., prior to reduction by growth of the microbial or mammalian cells.

After all of the test chemicals and stabilizing agents are disposed in the three receptacles, they are incubated together for an incubating time period associated with a preselected reading protocol. Generally the reading protocols which are available to use with this invention are a visible light reading protocol and a fluorescence excitation reading protocol. More details of these various reading protocols are given below.

After the incubating time period, the three receptacles are read in accordance with the preselected reading protocol to determine the presence or absence of growth of the microorganism or mammalian cells in the test well on the basis of the relative concentrations of resazurin (oxidized-blue) and resorufin (reduced-red) therein. The visible light reading protocol includes a decision algorithm based on at least one predetermined functional combination of the visible light reflectance color detected in each of the three test wells. The fluorescence excitation reading protocol includes a decision algorithm based on at least one predetermined functional combination of the values of the fluorescence emission signal produced by the reduction product resorufin in each of the test wells. The details of the reading protocols in accordance with this invention are given below.

In the method and apparatus of this invention, resazurin is used as a reduction/oxidation indicator. When microorganisms and mammalian cells grow in a growth medium, they convert nutrients to energy, resulting in a chemical reduction of their environment. An oxidation/reduction indicator which is present in the environment of the growing microorganism or cells will also be reduced. Thus, the use of an oxidation/reduction indicator with an appropriate oxidation potential range provides a universally applicable test for growth of all microorganisms and mammalian cells. Resazurin is such an oxidation/reduction indicator and is reduced to resorufin. Resazurin is deep blue in reflected color and nonfluorescent. Resorufin is red and highly fluorescent. This reduction of resazurin to resorufin is the basis for the visible light reading protocol and the fluorescence excitation reading protocol utilized in the method of this invention.

Prior art fluorescence reading systems for susceptibility testing do not incorporate a universal indicator of microorganism growth. Instead, they use fluorescent substrates which measure production of specific enzymes, and there is no one fluorescent substrate that will be utilized by all microorganisms. Resazurin reduction is not an enzyme based reaction but rather a chemical reaction depending on a change in the oxidation/reduction state of the environment. It is independent of enzymatic reaction.

Resazurin is also a pH indicator, having a blue color above a pH of about 6.5 to 6.8 and being red below that range of pH values. For this reason, it is important that the pH of the test chemical group in the growth control and test receptacles be controlled to provide the appropriate initial conditions, especially where the antimicrobial product has a relatively low pH (acidic). For that reason, it is preferred to add a selected pH buffer, such as a mixture of sodium dihydrogen phosphate and sodium hydrogen phosphate, to the set of test chemicals in the wells. The use of such phosphate buffer is further preferred since it has been found to inhibit certain antibiotics from turning red when dried on a solid substrate, as described in more detail hereinafter.

The visible light reading protocol used in accordance with this invention is based on the color shift from blue to red that is produced during the reduction of resazurin in the test well to resorufin as a result of microorganism growth. If there is growth of the microorganism in the test well 103, despite the presence of the preselected concentration of antimicrobial product disposed therein, then the test chemical solution present in the test well will turn from blue to red and a simple visual inspection of the test well provides a basis for determining a positive or negative test result. The growth control wells provide a basis for comparison of growth and no growth conditions to assist in identifying the condition of the test well.

FIGS. 2–5 illustrate in more detail the visible light reading protocol. FIG. 2 illustrates the initial condition of the test panel 100A prior to incubation. All three of the wells are blue in color as indicated by the shading in the area representing the wells.

The visible light reading protocol includes panel reading qualification algorithms which are used to determine whether the panel itself has failed to provide a proper basis for an accurate test or something has gone wrong and precludes achieving an accurate determination of organism growth or no growth in the test well. FIG. 3 illustrates a failed test due to a change in color of the negative growth control well from blue to red. Since no microorganism had been dispensed into that well, it should not have anything growing therein to produce the blue to red color shift from reduction of resazurin to resorufin. The negative growth control well may change slightly in the depth of blue color therein due to some autoreduction of resazurin by the growth medium during incubation (which is minimized by the measures described above), but change to a pink or red color indicates that the test has likely failed must be repeated. The color of the positive growth control well and the test well are not indicated in FIG. 3 since the color of these wells is not involved in this aspect of the panel qualification algorithm.

FIG. 4 illustrates a failed test due to the failure of the positive growth control well to show a color change from blue to red after incubation. The failure of the microorganism to grow in the positive growth control well where there is no growth inhibiting test chemicals present means that there is no reliable basis for judging whether growth of the microorganism in the test well has been inhibited or not by the concentration of antimicrobial product present there.

FIGS. 5 and 6 illustrate two test panels which have passed the panel qualification tests and also illustrate the algorithm for determining the final test result. In FIG. 5, inspection of the negative growth control well shows that it has remained blue in color as it should since no microorganism is supposed to be present in that well. The positive growth control well has shifted in color from blue to red as it should since the microorganism dispensed thereunto should be growing without any inhibition. In the test well 103, the color of the test solution is also still blue, indicating no organism growth in the test well. Accordingly, the test result is negative, i.e. no organism growth in the test well or test receptacle.

In FIG. 6, the negative growth control well and positive growth control well have the proper colors and the red color indicated in the test well produces a positive test result, i.e., there is organism growth in the test well that produced the color shift there just as in the positive growth control well.

It will be appreciated that the test panel 100 can easily be read manually, that is by looking at the wells with the naked eye to determine the test results assuming that the person doing the reading has the normal visual acuity for color recognition. In most cases of visual reading of the test panel 100, the panel will have been incubated for a sufficient period of time that the reduction of resazurin in the test well to resorufin will have proceeded to the point that the color shift from blue to red will be dramatic and easily discernable. However, in some cases of a weakly growing organism, or under conditions where the concentration of the antimicrobial product in the test well is just on the borderline of the MIC, the organism growth may be slowed to the point that the degree of color shift from blue to red is not strong. A color guide may be provided to aid in interpreting the test results and will illustrate the degree of color shift that must be present to call the test result positive or negative. Still there may be some conditions in which the test result will be indeterminate, i.e. it is impossible to judge visually whether there has been a color shift that indicates organism growth.

A particular advantage of the present invention lies in the ability to perform test protocols over extended periods of time. Since the stability of the resazurin in the control and negative test wells, as well as the resorufin in the positive test wells, is enhanced, the appearance of false negatives will be lessened or eliminated. Thus, additional incubation time for weakly growing organisms or cells can be provided to enhance the degree of color shift and facilitate recognition of positive test wells.

Figure 28:
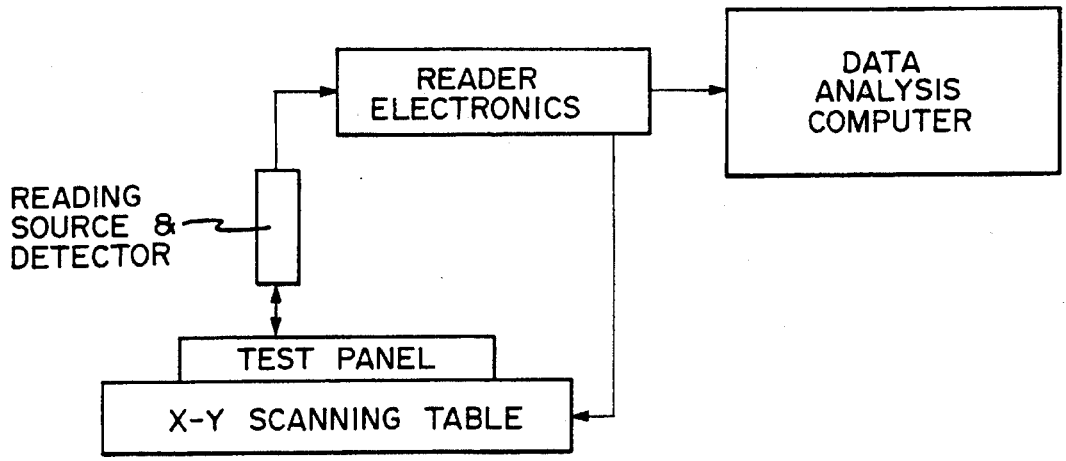
FIG. 28 is a schematic illustration of an automated panel reader system useful in accordance with this invention.
Figure 29:
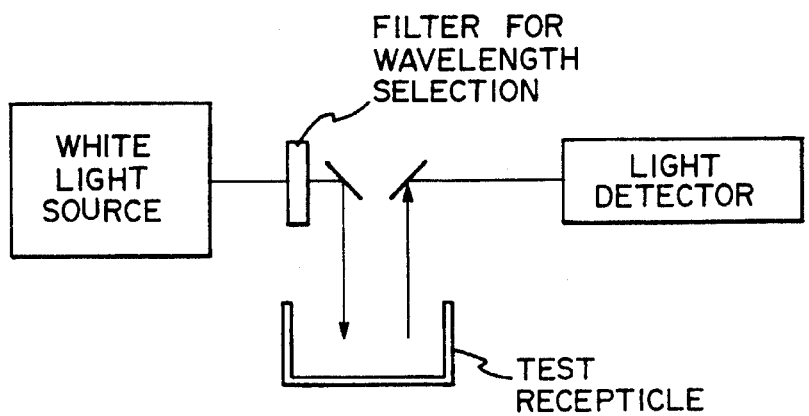
FIG. 29 illustrates a visible light reading system useful in connection with a visible light reading protocol for a test panel in accordance with this invention.

Automated reading of a test panel using the visible light reading protocol can also be readily achieved by instrumentation that is capable of colorimetric determinations. A schematic diagram of an automated colorimetric reading system is shown in FIGS. 28 and 29 for the case where the test panel is an opaque material and the white light source is above the panel. An alternative system in which the panel is clear and the white light source and filter are below the test panel could also be used.

As illustrated in FIGS. 28 and 29, in each case the test panel 100 is scanned relative to the light source and detector so that each of the wells 101–103 is read in sequence. After data on the color of the test solution in each of the three wells are obtained, the algorithms of the visible light reading protocol are applied to the data. First, the panel qualification algorithms are applied in the same manner as in the visual reading approach above, and then the test well data is examined to determine the final test result if the qualification tests are passed. With automated reading, it may be possible to accurately quantify the respective degrees of color difference between the test well and the negative growth control well and between the test well and the positive growth control well and to use that quantified data as the basis for determining the test result. The algorithm in this case may be very similar to the fluorescence excitation reading protocol which is discussed below.

Since resazurin is non-fluorescing and resorufin is strongly fluorescing at a wavelength of 580 nanometers, the test panel 100 may be read using a fluorometer in accordance with a fluorescence excitation reading protocol using a reading system illustrated schematically in FIG. 29. An excitation source having a wavelength at 560 or below is used to excite fluorescence emission from resorufin in the wells. Adequate separation of excitation and emission wavelengths should be maintained. Each test well 101–103 of the test panel 100 is scanned with respect to the exciting light source and detector so that the value of fluorescence excitation of resorufin in each of the three wells is obtained. For purposes of this explanation, the value obtained from the negative growth control well is designated N, the value from the positive growth control well is designated P, and the value from the test well is designated T. This reading of the panel is done after incubation of the test panel has been done for a period of time sufficient to cause a substantial production of resorufin in wells in which organism growth is occurring, usually at least 3 hours and preferring 5 hours, or more with a particularly useful protocol relying on overnight incubation of the cellular sample. The values of N and P are then examined to determine if the data correspond with a valid test. The value of N is compared with, and for valid panel data must be below, a threshold value Nf which has been determined to be indicative of a failed test due to the presence of too much resorufin in the negative growth control well due to contamination of the panel or some other cause. The value of P is compared with, and for valid panel data must be above, a threshold value Pf which has been determined to be indicative of a failed test due to the presence of too little resorufin in the positive growth control well after the incubation period due to a failure of the growth medium to promote organism growth or other causes. If the panel data passes these validation tests, then the test well data can be operated on in accordance with the rest of the fluorescence excitation reading protocol.

A growth control parameter Gc is preferably calculated as the difference in the values of P and N. Similarly a corrected test parameter Tc is preferably calculated as the difference in the values T and N. The value N obtained from the negative growth control well is thus treated as a background value of resorufin that may be present in the other two wells due to some autoreduction of resazurin during the incubation process.

The next step in this reading protocol is to calculate the value of a test variable I using a prearranged functional combination of the values of Gc and Tc. This functional combination could be simply the difference between the two values, but it is preferable to use a function that includes the ratio of Tc and Gc. After the value of the test variable I has been calculated, it is subjected to a decision algorithm and a test result is reported based on the outcome of application of the decision algorithm.

The decision algorithm is based on data obtained from controlled tests on test panels using organisms or cells that produce known test results. For example, the decision algorithm may involve a predetermined positive decision value XP and a predetermined negative decision value XN. These decision value are based on data collected from organisms that behave in a known manner with the value XP selected such that all such known organisms produce a value of the test variable I which is greater than or equal to XP if the organism is growing in the test well or which is less than or equal to XN if the organism is not growing in the test well. The spread between the positive and negative decision values is an indeterminate range and an indeterminate test result will be reported in the value of I is between those two decision values.

The above described fluorescence excitation reading protocol is basically a static single reading protocol that is done after a predetermined incubation time period associated with the protocol. A more complex, and potentially more accurate fluorescence excitation reading protocol would involve the use of a preliminary panel reading qualification tests that is required a minimum value difference between P and N, i.e. a minimum value of Gc before the test parameter I is calculated. If the panel passed the other data qualification tests on the P and N values as discussed above, but the value of Gc is below the preset limit, then the panel would be incubated for an additional time period to allow the value of Gc to increase (if it can) with the passage of time. Such a modified approach will give test results of greater accuracy and increase likelihood of avoiding an indeterminate test result for organisms that are slow growing in the positive growth control well even though no antimicrobial or cytotoxic product is present.

The method of this invention is adaptable to a rapid determination of microorganism or cellular growth in the test well using a fluorescence excitation reading protocol that is based on determining the dynamic characteristics of the changes in the resorufin content of the growth control wells and the test well. These dynamic characteristics may include the rate of change of the amount of resorufin in these wells (i.e. the velocity of resorufin production) and the rate of change in this rate of change with time (i.e. the acceleration of resorufin production) in the wells.

In test wells in which the microorganism is growing, the number of such microorganisms will increase exponentially with time, producing a corresponding exponential increase in the amount of resorufin in the test well. In test wells in which the microorganism is not growing, some autoreduction of resazurin to resorufin may be occurring (although inhibited by the measures described above), but this occurs at a linear rate and is thus readily distinguishable from growth related resorufin production.

The incubation step in this method involves incubating the three test wells or receptacles together for a time period sufficient to produce a value of a dynamic characteristic of resorufin production in the positive growth control well that exceeds a predetermined panel qualification value. The value of this dynamic characteristic is determined by reading the value of fluorescence excitation of resorufin in both the positive growth control well and the negative growth control well in at least two separate time periods required for both velocity and acceleration characteristics to be determined. If the value is below the qualification value, the panel is returned for a predetermined further incubation time period after which the values of fluorescence excitation of resorufin are again obtained and the panel qualification test is rerun. This continues until the panel qualifies for reading or it is determined from the data that the panel is defective and will never qualify for reading.

After panel reading qualification tests are passed, the values of the dynamic characteristics of resorufin production already measured are used to calculate values for dynamic production of resorufin in the positive growth control well and the test well by performing additional measurements after one more time period or by using the data values already obtained. The value for the test well is designated T' and the value for the growth control wells is designated G'. The use of these designations with the "prime" signs is not intended to limit the dynamic characteristics to velocity determinations which might be suggested by a strict mathematic interpretation of the use of the "prime" designation. It should be understood that both rate of change and acceleration in rate of change may be used in the values T' and G'.

After these values are determined, the value of a test variable I is calculated as a prearranged functional combination of T' and G', preferable a function including the ratio of these two parameters. Then a test result is reported using the value of the test variable in a preselected decision algorithm. The decision algorithm may utilize predetermined positive and negative decision values XP and XN as used in the visible light reading protocol. Again these values are determined empirically from data obtained in controlled tests using organisms that produce known test results.

FIG. 7 illustrates that the general method of this invention is preferably carried out by forming a test module in each of the growth control wells 101 and 102 and the test well 103. As shown, test modules 107 and 108 formed in each of the growth control wells with the test module in each case being a type TMA.

A test module 109 is formed in the test well 103 and is of type TMB indicating that it has a different set of test chemicals therein. Each of the test modules 107 and 108 has a test chemical subset TCB1 therein and the test module 109 has this same test chemical subset plus the antimicrobial or cytotoxic product. The test chemical subsets comprises dry solid volumes of a subset of the constituents of a set of test chemicals which preferably include all of the test chemicals described above, namely resazurin, growth medium, buffer, and redox stabilizers.

After the test modules are formed in the wells, they are rehydrated by dispensing a volume of liquid into each well. The negative growth control well 101 is rehydrated with a volume of liquid 110 containing only the test chemical subset TCB2. Both the positive growth control well and the test well are rehydrated with volumes of liquid 112 and 113 in inoculator 111 which contain the microorganism or cells as well as the test chemical subset TCB2. The division of the test chemicals between the test modules and the rehydrating liquid illustrates that there is substantial flexibility in the method of this invention in the process of achieving the final test chemical solution in each of the wells prior to the incubation step. The preferred set of test chemicals can be divided into various subsets with one subset in the test module and the other subset in the rehydrating solution. The preferred method involves placing all of the test chemicals in the test modules in the wells so that the rehydrating liquid is simply a volume of sterile liquid for the negative growth control well and a volume of the same liquid with a dispersion of the microorganism therein as an inoculum for the other wells. It should be understood that the test modules could be rehydrated and inoculated in separate steps.

In the preferred method, the test chemical subset in each of the test modules in the growth control wells is the same. However, it should be understood that the method of this invention could be implemented using a different test chemical subset in the negative growth control well from that in the positive growth control well. It would also be possible to use different test chemicals subsets in the positive growth control well and the test well, but this would complicate the preparation of the rehydrating inoculum liquid and thus is not the preferred approach.

Figure 8:
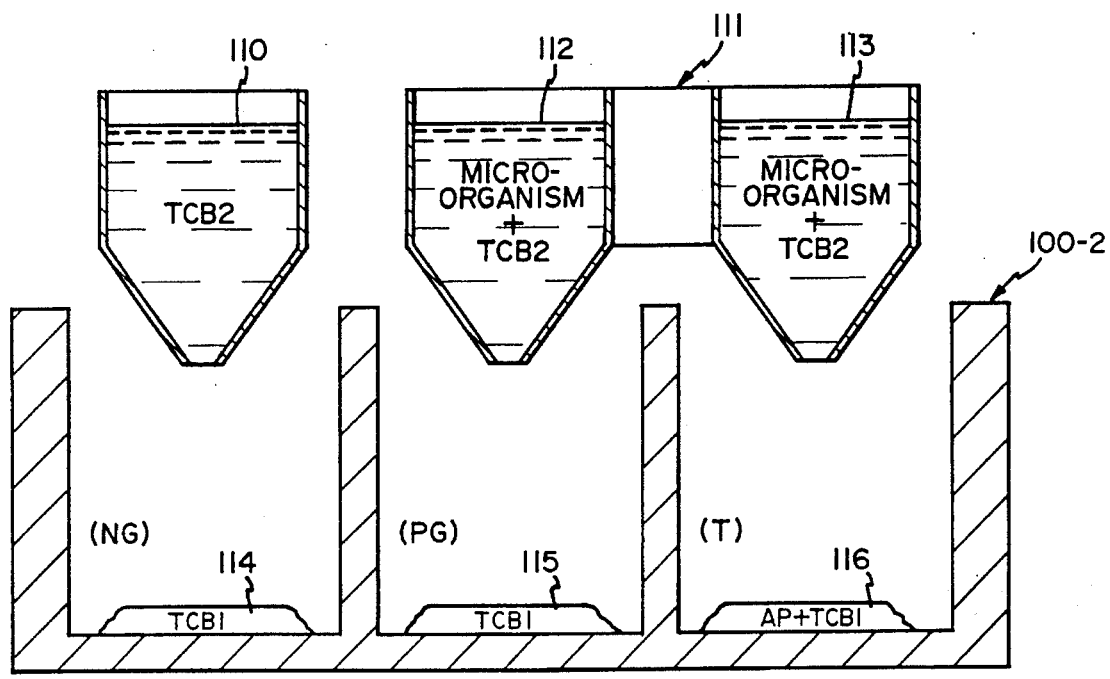

As illustrated in FIG. 8, the test modules in the wells may take the form of a dry solid volume of the test chemicals formed directly on the walls of the wells of the panel 100-2 itself. This can be implemented by dispensing the constituents of the test chemical subset TCB1 into each of the growth control wells and that subset plus the antimicrobial product into the test well and then drying the panel, e.g. in a freeze drier, to capture the test chemicals as a dry solid volume on the walls of the wells.

Figure 9:
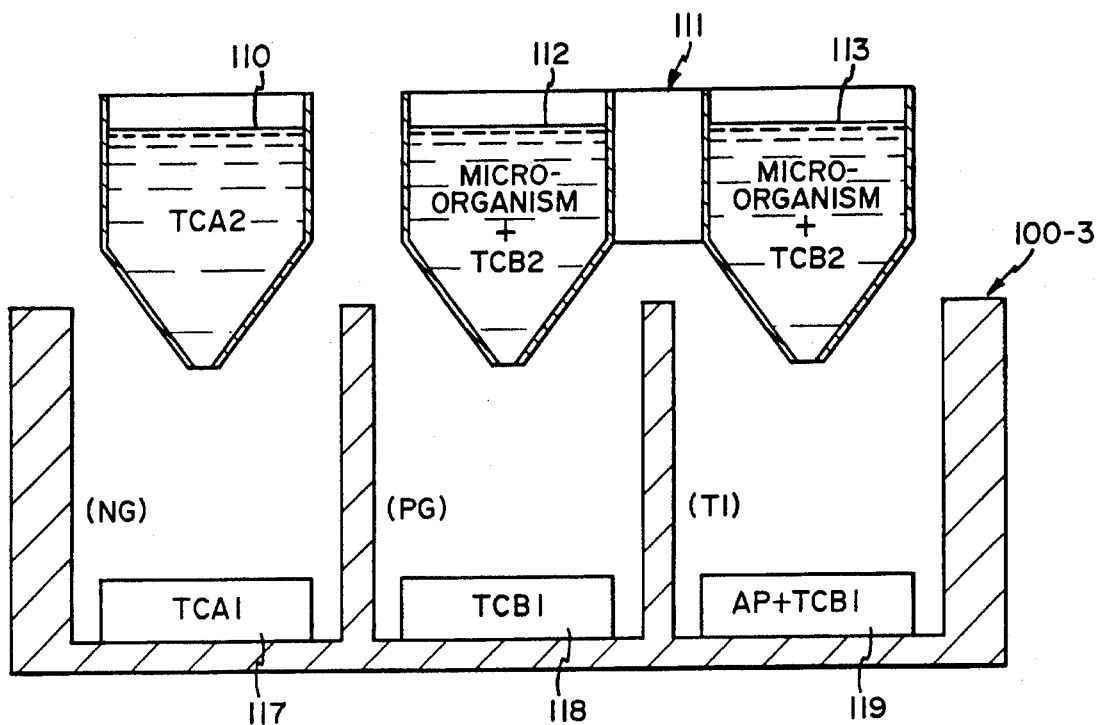

FIG. 9 illustrates that the test modules formed in the wells may take the form of a carrying medium such as the carrying media 117, 118, and 119. The preferred form of the carrying medium in each case is an absorbent paper disk of the same type as is used in the disk diffusion testing described above. Other forms of carrying media may also be used if they have generally comparable characteristics to the absorbent paper disks. The carrying media needs to be capable of being dispensed in a convenient way for manufacture of the test panels.

Figure 10:
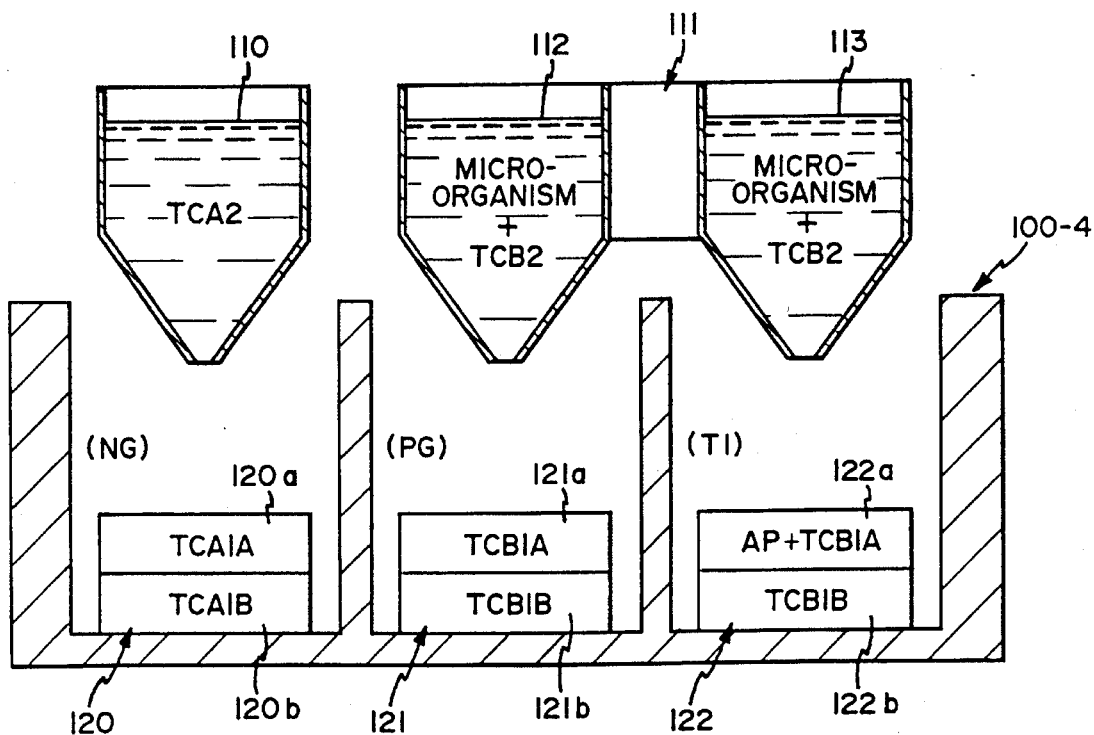

A process for preparing test modules using absorbent paper disks is described below. In FIG. 9, the a single carrying medium is used in each well, whereas in FIG. 10 a two carrying media are used in each well, with each carrying medium having a portion of the subset of test chemicals formed in the test module carried therein. This illustrates that it is possible, for example, to implement the method of this invention by using two absorbent paper disks, one carrying the resazurin and the other the growth medium. This approach avoids the interactions between these two tests chemical constituents in the process of forming the test modules in the wells and especially during the drying of the disks.

FIGS. 11–14 illustrate the application of the principles of this invention in qualitative susceptibility testing apparatus, i.e. testing for the qualitative susceptibility of a microorganism or cells to growth inhibition by an antimicrobial or cytotoxic product utilizing a prearranged qualitative susceptibility testing protocol involving first and second quantities of the antimicrobial or cytotoxic product. A test panel 200 defines a negative growth control well 201, a positive growth control well 202 and a pair of test wells 203 and 204. A test module 205 is carried in each of the growth control wells. Test modules 206 and 207 are carried in the test wells.

Figure 11:
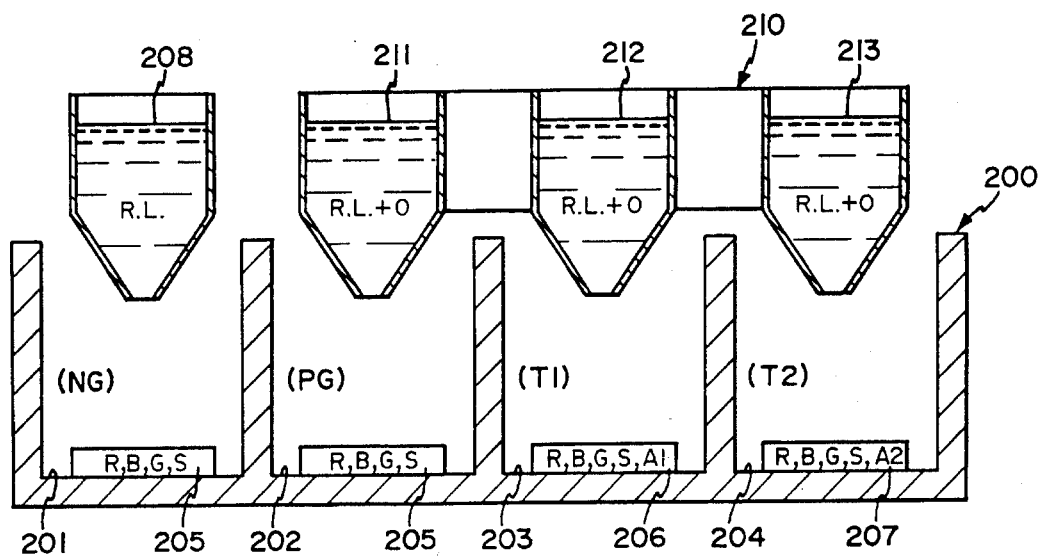
FIG. 11 illustrates use of the method and apparatus of this invention in a qualitative susceptibility test panel.
Figure 12:
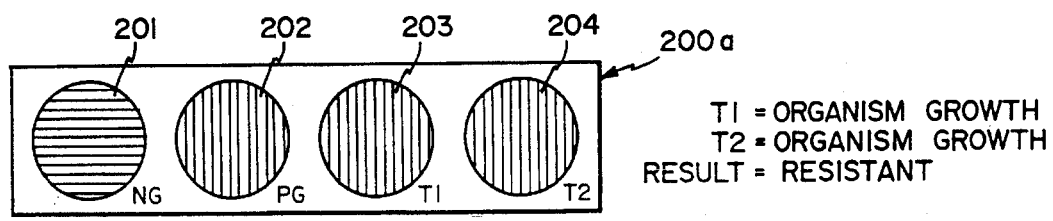
FIGS. 12–14 illustrate a visible light reading protocol for the qualitative susceptibility test panel of FIG. 13.

FIG. 12 illustrates the preferred form of the invention in which the test modules have all of the chemical constituents of the set of test chemicals therein, but it should be understood that the test chemicals may be divided between the test modules and the rehydrating liquid volumes as previously described. FIG. 11 also illustrates the use of a single absorbent paper disk as a carrying medium forming the basis of each test module, but it should be understood that any of the forms of test modules previously discussed could also be used in the qualitative susceptibility testing apparatus in accordance with this invention.

Each of the test module is labelled as containing R for resazurin, B for buffer, G for growth medium and S for redox stabilizer. In addition, test module 206 contains a first quantity of the antimicrobial or cytotoxic product designated A1 and test module 207 contains a second quantity of the antimicrobial or cytotoxic product designated A2. For this description, we will consider A2 as the higher of the two concentrations of antimicrobial product in the qualitative susceptibility testing protocol.

Test module 201 in the negative growth control well is rehydrated with a volume of rehydrating liquid portion 208 forming part of an overall inoculating system 210. Each of the test modules 205, 206, and 207 is adapted to be rehydrated with a volume of rehydrating liquid together with a suspension of the microorganism to form the inoculum for those wells. After rehydration, test panel 200 is placed in an incubator for a prearranged incubation time period associated with a preselected reading protocol to be used with the panel.

Figure 13:
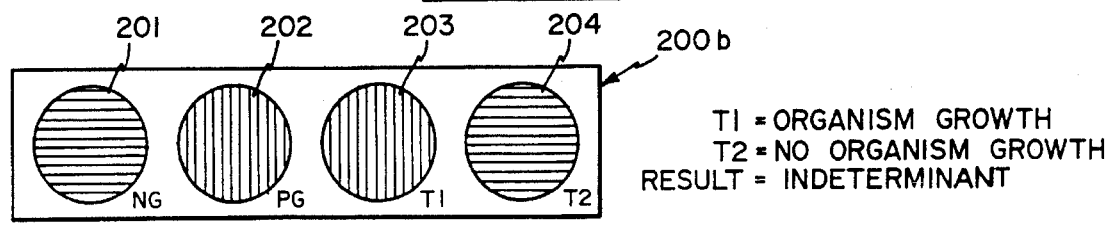
Figure 14:
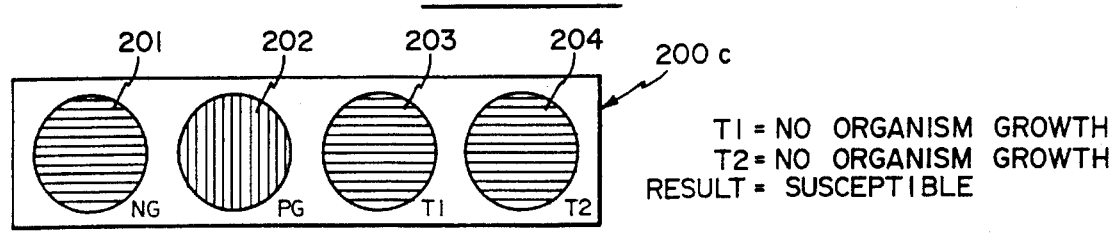

FIGS. 12–14 illustrate a visible light reading protocol for test panel 200. It should be understood that all of the manual and automated reading protocols described above could be applied to the reading of panel 200.

Referring back to FIGS. 2–4, it should be understood that the pre-incubation color in all of the wells of the test panel is blue. Also the same panel reading qualification tests are applied using the negative growth control well and the positive growth control well. These are not repeated here to avoid redundancy and this description assumes that the panel has passed qualification tests for accurate reading with the negative growth control well showing blue color and the positive growth control well showing red color.

In FIG. 12, the panel 200A shows red color in both of the test wells 203 and 204 indicating organism growth in both wells. The corresponding test result of this qualitative susceptibility testing is that the microorganism or cells tested is resistant, i.e. it is not susceptible to growth inhibition by the higher concentration A2 of antimicrobial or cytotoxic product in test well 207. In FIG. 13, the panel 200B shows red color in test well 203 indicative of organism growth, but blue color in test well 204 indicative of inhibition of growth. In this case the result is indeterminant since the microorganisms or cells are neither sensitive or resistant. The use of the term indeterminant should not be misunderstood as failing to give information on the qualitative susceptibility of the microorganism. This test result merely means that the organisms or cells are neither highly susceptibility or highly resistant. This gives the referring physician an indication that in the case of microorganisms, successful drug therapy may be achieved with that antimicrobial product, in fairly high concentrations.

In FIG. 14, the panel 200C shows blue color in both of the test wells 203 and 204 indicative of inhibition of growth of the microorganism in both test wells. The corresponding test result is "susceptible" indicating that the microorganism or cells can be inhibited in growth by relatively low concentrations of the antimicrobial or cytotoxic product.

FIGS. 15–17 illustrate the application of the principles of this invention in quantitative susceptibility testing apparatus, i.e. testing for the quantitative susceptibility of a microorganism or cells to growth inhibition by an antimicrobial or cytotoxic products utilizing a prearranged quantitative susceptibility testing protocol involving N different quantities of the antimicrobial or cytotoxic product where N is greater than two, and is typically six or more. The current FDA standard for quantitative susceptibility testing is a minimum of five dilutions of the antimicrobial product covering some portion of the therapeutic human dosage range.

Test panel 230 defines a negative growth control well 231, a positive growth control well 232 and, in this case, four test wells 233–236. Four test wells are used here for convenience of illustration. The use of a larger number of test wells will be discussed below in connection with testing kits that incorporate the quantitative susceptibility testing principles of this invention. A test module 237 is carried in each of the growth control wells. Four different test modules 238–241 are carried in the four test wells. As with the above description of qualitative susceptibility testing, the test modules here illustrate the preferred form of the invention using a single carrying medium in the form of an absorbent paper disk with all of the constituents of the set of test chemicals carried in each of the test modules and with the test modules in the test wells also carrying four different quantities of the antimicrobial or cytotoxic product, namely A1–A4. For purposes of this description, the amounts of the antimicrobial product will be considered to be increasing from A1 to A4. It should be understood that any of the alternative forms of the invention as described above in connection with FIGS. 7–10 could also be used here.

Test module 231 is rehydrated with a volume of rehydrating liquid 242 forming a portion of an overall inoculation system 245. Each of the test modules in the other wells is rehydrated with a volume of rehydrating liquid to which a preselected quantity of the microorganism has been added with individual inoculation volumes 246–250 of mammalian cells for the wells. A specific form of inoculation system will be described below in connection with a test kit embodiment of this invention. After rehydration and inoculation, panel 230 is placed in an incubator for a prearranged incubation time period associated with preselected reading protocol to be used with the panel.

FIGS. 16 and 17 illustrate a visible light reading protocol for test panel 230. It should be understood that all of the manual and automated reading protocols described above could be applied to the reading of panel 230.

Referring back to FIGS. 2–4, it should be understood that the pre-incubation color in all of the wells of the test panel is blue. Also the same panel reading qualification tests are applied using the negative growth control well and the positive growth control well. These are not repeated here to avoid redundancy and this description assumes that the panel has passed qualification tests for accurate reading with the negative growth control well showing blue color and the positive growth control well showing red color.

As shown in FIG. 16, panel 230A shows a color shift from blue to red in each of the first three test wells 233–235 indicative growth of the microorganism or mammalian cells in each of these test wells. Test well 236 shows the original blue color indicative of no growth of the microorganism or cells in that test well. The test result obtained from this reading is that the MIC of the antimicrobial or cytotoxic product used in the test panel is the concentration A4. It should be understood that the concentration A4 refers both to the quantity of the antimicrobial or cytotoxic product in the test module and to the concentration of the antimicrobial or cytotoxic product in the final test solution after inoculation and rehydration of the test chemicals.

As shown in FIG. 17, panel 230 B shows a color shift from blue to red only in the first test well 233 and the original blue color is present in the other three test wells 234–236. This indicates growth of the microorganism or cells only in the first test well and inhibition of growth in the other three for a resultant MIC value of A2. A2 is the MIC value since the test shows A2 as the lowest concentration of the antimicrobial or cytotoxic product which inhibits growth of the microorganism or cells.

FIGS. 18–21 illustrate qualitative susceptibility test kits according to this invention and also show how components of the test kits are used in performing the method of this invention. For completeness, FIG. 18 shows a primary culture plate 255 on which colonies of the microorganism to be tested may be grown, but this primary culture plate is not considered a part of the test kit of this invention. The components of test kit 260 shown in FIG. 20A are a container 261 of rehydrating liquid, an inoculum preparation tray 262, an inoculator system 263 and a test panel 264 in which the test wells are preloaded with appropriate test modules as previously described.

The rehydrating liquid in container 261 contains the subset of test chemicals TCB2 that are not in the test modules in the wells of the panel 264 as previously described. In the preferred embodiment, all of the test chemicals in the set are in the test modules and the rehydrating liquid is a preselected sterile liquid such as distilled water. It may also comprise 0.9 percent sodium chloride solution and may include a variety of wetting agents to assist in producing a uniform suspension of the microorganisms.

Inoculum preparation tray 262 may be formed in a convenient shape for mixing the rehydrating liquid with microorganisms from colonies growing on the primary culture plate to form the inoculum for the positive growth control well and the test wells T1 and T2. The configuration of the inoculum preparation tray needs to be adapted to the structure and operation of the inoculator system 263. Inoculator system 263 may comprise a standard multi-tip pipetter system or it may be especially designed for dispensing inoculum into the wells of the test panel. As shown, the inoculator system includes an inoculator means for dispensing rehydrating liquid into the negative growth control well and means for dispensing inoculum into the positive growth control well.

Test panel 264 carries preloaded test modules as shown, with two test wells for qualitative susceptibility testing using a single antimicrobial product in this case. The test kit is designated QLS-1-A indicating qualitative susceptibility testing with one antimicrobial product. FIG. 19 illustrates a preloaded test panel 275 useful for qualitative susceptibility of a microorganism using M different antimicrobial or cytotoxic products with a pair of test wells associated with each antimicrobial or cytotoxic product and preloaded with test module having appropriate concentrations of the antimicrobial cytotoxic product. As shown in FIG. 14, each of the test modules is preferably a single absorbent paper disk which is labelled with a visually readable legend designating the name of the antimicrobial or cytotoxic product in the test module and the concentration of that antimicrobial or cytotoxic product therein. The designation A1 represents the name of the first antimicrobial or cytotoxic product printed on the disk and the designation K1 represents the concentration printed on the disk.

FIG. 18 illustrates a test kit 270 designated QLS-1-B, in which a bare test panel 274 is used instead of a preloaded test panel as in kit 260. Additional components of kit 270 comprise a growth control test module dispenser 271 for dispensing test modules TMA 272 into the negative growth control well and the positive growth control well of panel 274 and an AP test module dispenser 273 for dispensing test modules TMB1 and TMB2 into the test wells T1 and T2. Dispenser 273 stores the two different test modules in alternate interleaved fashion so that two sequential actuations of the disk dispensing mechanism are involved in loading the two test wells. The dispenser 271 and 273 may be standard antibiotic disk dispensers loaded with test module in accordance with this invention in the form of absorbent paper disks.

As an alternative to interleaved disk, single dispenser shown in FIG. 18, it should be apparent that two separate dispensers could be employed, each storing and dispensing one of the AP test modules into an associated test well. It should also be understood that kit 270 may comprise a multiplicity of test panels 274 to go with the dispensers which are capable of dispensing test modules into a number of test panels.

Test panel 274 is configured for testing with one antimicrobial or cytotoxic product. As shown in FIG. 70, a test panel 276 that defines a negative growth control well, a positive growth control well and a plurality of pairs of test wells for a plurality of antimicrobial or cytotoxic products could also be employed in the test kits of this invention. To load test panel 276, one dispenser of the type 271 is employed for the growth control wells and one dispenser of the type 273 for each of the antimicrobial or cytotoxic products is employed to load the test wells for each antimicrobial or cytotoxic product. For test panel 276 it would be preferable to provide a test module dispenser that is capable of loading an entire row of wells at one time.

FIG. 21 illustrates that the test kits of this invention for qualitative susceptibility testing of a microorganism or mammalian cell against multiple antimicrobial or cytotoxic products may utilize a panel 277 which includes both a preloaded panel section and a loadable panel section. A test kit with this type of test panel combines the convenience of preloaded test wells for antimicrobial or cytotoxic products that are conventionally used in virtually all testing situations with the flexibility of user selected antimicrobial or cytotoxic products for purposes of customizing a portion of the test panel with antimicrobial or cytotoxic products that are tailored to the needs of the user in connection with particular testing situations. Test kits with loadable tests wells are especially advantageous in providing for configuring test panels to include newer antimicrobial products as they are developed without waiting for such antimicrobial products to be included on preloaded panels from the manufacturer.

FIGS. 22–27 illustrate the quantitative susceptibility test kits according to this invention. Referring to FIG. 22, test kit 280 illustrated therein comprises a container 281 of rehydrating liquid, an inoculum preparation tray 282, an inoculator system 283 and a preloaded test panel 284. The form and function of these test kit components is generally the same as corresponding components already described in connection with the test kit in FIG. 18A and the description need not be repeated here.

FIG. 22B illustrates a test kit 290 similar to the kit 280 in FIG. 22A but employing a base test panel 294 and including test module dispenser 291 and 293. Dispenser 291 dispenses growth control test modules into the growth control wells of panel 294. Dispenser 293 dispenses AP test modules into the test wells of panel 294. As shown, dispenser 293 has the test modules for the four test wells stacked in order so that four sequential actuations of the dispenser are used to dispense four different test modules in the form of disks into the four test wells. FIG. 23 illustrates the alternative of using four separate dispensers 295–298 each containing a single type of AP test module with a single concentration of the antimicrobial product therein. These four dispenser can be operated individually or they may be combined in an overall dispensing system which holds all four dispensers in position for dispensing four disks simultaneously and has a single actuator mechanism that operates the dispensing finger in each dispenser at the same time.

FIG. 24 illustrates a preloaded test panel 300 defining a negative growth control well, a positive growth control well and a M column by N row array of test wells with each column associated with one of a plurality of antimicrobial products and being preloaded with test modules having appropriate antimicrobial products and different concentrations as indicated. FIG. 25 illustrates a corresponding loadable test panel 301 having the same overall testing capability. As shown in FIG. 26, M individual dispensers 302–306, each having a sequential stacking of AP test modules associated with user selectable antimicrobial products may be employed to load test panel 301.

FIG. 27 illustrates a test panel 310 having an M1 by N array of preloaded test wells and an M2 by N array of loadable test wells The test module dispensers shown in FIG. 26 may be used to dispense AP test modules into the loadable test well section of the panel 310. Test panel 310 provides the same advantages in the quantitative susceptibility testing area as the test panel 277 for the qualitative susceptibility testing area as described above. The multiwell test panels used in connection with this invention are preferably formed from a white, opaque plastic material. Such panels allow use of lower concentrations of resazurin for both visible light reading and fluorescence reading. Lower concentrations of resazurin are less toxic to microorganisms and thus minimize potential influence of resazurin on test results. Light intensity reflected from the white walls of the panel increases the signal available in both visible light and fluorescence reading. The white panel provides a uniform reading background which eliminates any need for background lighting equipment for reading the panel and results in more consistent and accurate visual interpretations. Smaller differences in color can be discerned with white background.

White panels can be manufactured with less expensive plastics and plastic panel forming technology because optical clarity is not a requirement.

If this invention is used in frozen panels, the test wells may simply be inoculated with a multiprong inoculum transfer devices which transfer a small volume (5–10 ml) from an inoculum seed trough to each test well in the panel.

If this invention is used in dried panels, there are two optional approaches to inoculation. All of the wells of the panel can first be rehydrated with a volume of rehydrating liquid that has no microorganism in it. Then inoculation of the test wells is performed as described above in connection with the frozen panel.

Alternatively, rehydration and inoculation can be done simultaneously by first putting a prearranged concentration of the microorganism in the rehydrating liquid and then dispensing a consistent volume of this inoculum liquid into each test well. This can be done with a single tip pipettor, a multitip pipettor, or with a special delivery system custom designed for this purpose.

The preferred form of this invention involves placing all of the components of the set of test chemicals, i.e. resazurin, growth medium, buffer (if needed), and redox stabilizer into a test module in the test wells of the panel. To simplify the overall description here, the discussion of processes of making the test modules and panels incorporating test modules will be limited to this approach.

To incorporate the method and apparatus of this invention in frozen test panels, the resazurin together with appropriate stabilizing components of the test chemical group are dispensed into the test wells either together with the growth medium and antimicrobial product dilutions or separately.

The process of forming test modules in dried panels is the same as for frozen panels except the test chemical constituents are dried in the wells to form a test module in the form of a dry solid volume on the walls of the wells themselves. Drying can be done with forced air or in vacuum. The formulation of the test chemical components is more critical when the test module is in dried form since the concentrations of the resazurin, antimicrobial product and growth medium become very high as drying nears completion. Adequate buffering of the pH of the solution and stabilization of the reducing action of the growth medium is important under these circumstances. The chemical formulations described below for used in the process of manufacturing test modules in the form of absorbent paper disks are preferably used in dried panels to reduce the volume of liquid in the test wells that must be dried.

There are various approaches that can be taken to manufacturing paper disks with the components of the test chemical set captured in dried form in the disk. Generally, for large volume manufacturing, sheets of the paper disk media preprinted with the legend identifying antimicrobial or cytotoxic product and concentration will be batch impregnated with the test chemical solution, dried, and then cut into disks and packaged. In the case of stacked, serial dilution disk packaging, stacks of paper media with the different concentrations of the antimicrobial product are preferably cut into disks in one operation and then packaged.

To manufacture disks in small volumes, the following process can be employed. A volume of the disk loading solution is made up. Since the paper disks are capable of holding only 25 microliters of the solution and the final volume of the rehydrating liquid in the test wells is conveniently 100 microliters, a four times concentration of the test chemicals is used in the disk loading solution.

Specifically, the following disk loading solution is prepared. The basic carrying solution is phosphate buffer of pH 7.4 in 0.1 molar concentration. The growth medium, which is standard Mueller-Hinton broth in dry powder form, is added at 88.0 grams per liter. Resazurin is added to achieve a concentration of 0.06 grams per liter, and methylene blue is added to achieve a concentration of 0.01 gram per liter. Potassium ferricyanide (0.132 gram per liter; 0.0004M) and potassium ferrocyanide (0.169 gram per liter, 0.0004M) are added to serve as a redox stabilizer. This solution is then used as the diluent for the antimicrobial product to be included in the test module disk. The initial concentration of the antimicrobial product is also four times the final concentration desired in the test well after rehydration, but is adjusted to correct for irreversible binding of the antimicrobial product to the disk. In other words, when the dried test chemicals in the disk are rehydrated, the entire amount of antimicrobial product does not enter the rehydrating liquid. The bound antimicrobial product in the disk is not active against the microorganism.

The concentration of resazurin is selected to produce a bright blue starting color for high visual contrast between positive and negative growth of the microorganism. Higher concentration of resazurin would having increasing toxicity for some microorganisms and would decrease or delay the discernable visual color change in response to growth of the microorganism. Lower concentration of resazurin would result in poor contrast between positive and negative test well reactions, i.e. the color in wells where the microorganism is growing to a slight extent would not be as readily discernable as a color change. These statements all pertain to visual reading of the test panels and the concentration of resazurin is less critical for fluorescence excitation reading protocols.

The concentration of growth medium is the standard concentration used in these types of test panels and there is no reason to change this. A decrease in concentration will decrease growth rates and an increase does not increase growth rate, but exacerbates the autoreduction tendency of the growth medium during incubation and drying. It should be understood that other growth medium formulations than the standard Mueller-Hinton could also be used, but they must meet the performance characteristics of the now standard Mueller-Hinton broth.

The buffer is used in sufficient concentrations to prevent pH shifts and accompanying color non-uniformity between test wells or test modules due to high concentrations of acidic antimicrobial products especially during the drying process. The pH 7.4 is used because it is the recommended pH for Mueller-Hinton broth when used in this application. Concentration of buffer is kept at the minimum required to provide stability of pH especially during drying. Too high a molar concentration is to be avoided because it can delay the reduction of resazurin to resorufin and adversely affect the consistency of test results.

The redox stabilizer is used in sufficient concentration to suppress autoreduction of the resazurin during the drying and incubation processes to acceptable levels. The poising pair ferricyanide/ferrocyanide was selected for its relative low toxicity to microorganisms and its stabilizing capacity in the appropriate oxidation/reduction potential range. Concentration is selected to avoid excessive stabilization of the oxidation/reduction reaction due to microorganism growth since that would delay and/or adversely affect accuracy of test results.

The process of loading the disk loading solution in the disks involves aseptic processing using sterile raw materials. A group of disks is placed in a single layer, without edges touching, in a flat, sterile, container which can be covered, such as a covered Petri dish. A micropipette is used to dispense 25 microliters of the disk loading solution onto each disk.

The container is then covered and placed in a freezer at −70° Centigrade overnight. The container is then transferred to a freeze drying chamber and the disks are dried in vacuum. They are then removed, placed in capped vials containing a desiccant capsule and stored in a dark refrigerated environment.

For loading disks into test receptacles, the disks are transferred individually in an aseptic manner. It should be understood that this method can be used for small volume production of test panels for use in clinical testing and the like, but large scale automated production of disks and automated panel loading technology would be employed for manufacturing preloaded test panels in volume.

FIG. 28 illustrates the general components employed in an automated reader system for reading test panels which incorporate the methods and apparatus of this invention using either the visible light reading protocol or the fluorescence excitation reading protocol. After incubation the test panel is placed on a scanning table which places each test well in place to be read by the reading source and detector together with the reader electronics. The data from the reader electronics is preferably communicated to a data analysis computer where the algorithms of the associated reading protocol are applied to the data from each well in the test panel.

Figure 30:
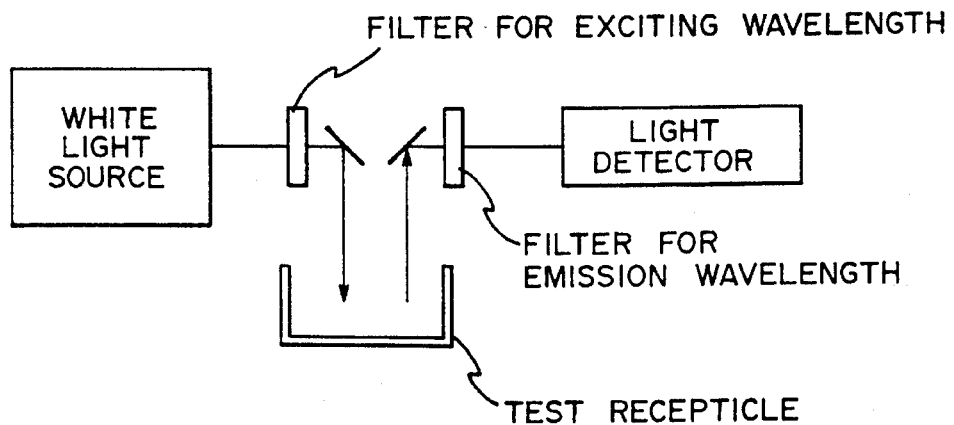
FIG. 30 illustrates a fluorescence excitation reading system useful in connection with a fluorescence excitation reading protocol for a test panel in accordance with this invention.

FIG. 29 shows that, in the case of visible light reflectance reading for implementing a visible light reading protocol, a single filter may be used for selection of the reading wavelength which will be used to determine the reflected color characteristics of the liquid in the test well. Multiple wavelength analysis could also be used if desired. FIG. 30 illustrates that, in the case of fluorescence excitation reading for implementing a fluorescence excitation reading protocol, separate filters are employed for selecting the exciting wavelength and the emission wavelength. Both visible light reading of reflected color and fluorescence reading can be implemented with instrumentation that is currently commercially available and known to persons familiar with this technology.

Figure 31:
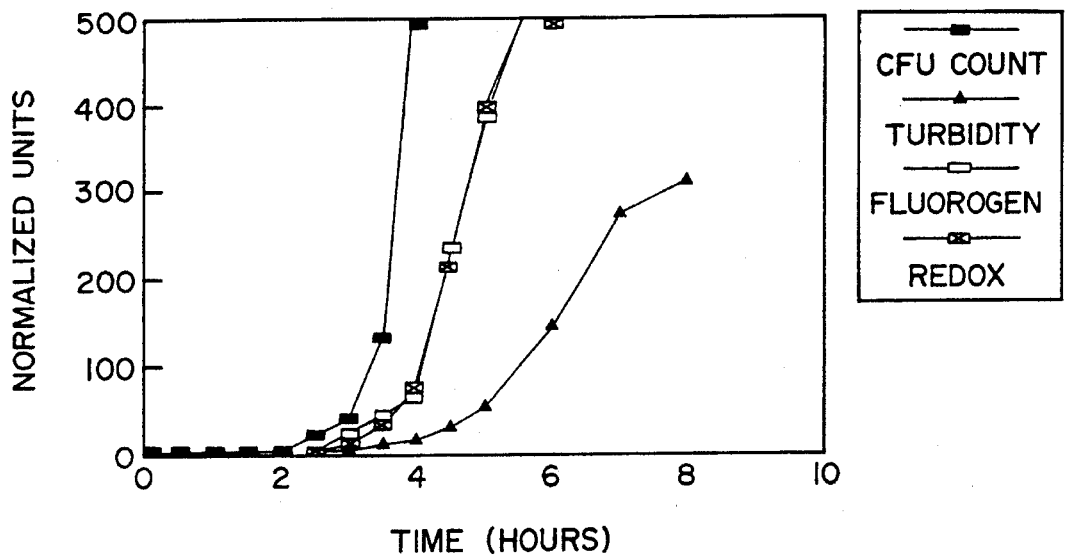
FIG. 31 is a graph showing the results of fluorescence reading of microorganism growth in a test well in accordance with the method of this invention compared with other prior art reading methods.

FIG. 31 illustrates that the fluorescence excitation reading of microorganism growth using the resazurin redox reaction in accordance with this invention provides data generally comparable to fluorogenic reading used in prior art rapid microorganism growth detection systems in cases where the particular microorganism is well adapted to detection by the fluorogenic detection system. The fluorescence excitation reading approach of this invention will be superior to the fluorogenic reading of the prior art for microorganisms that are not readily detected by such prior art methods.

Figure 32:
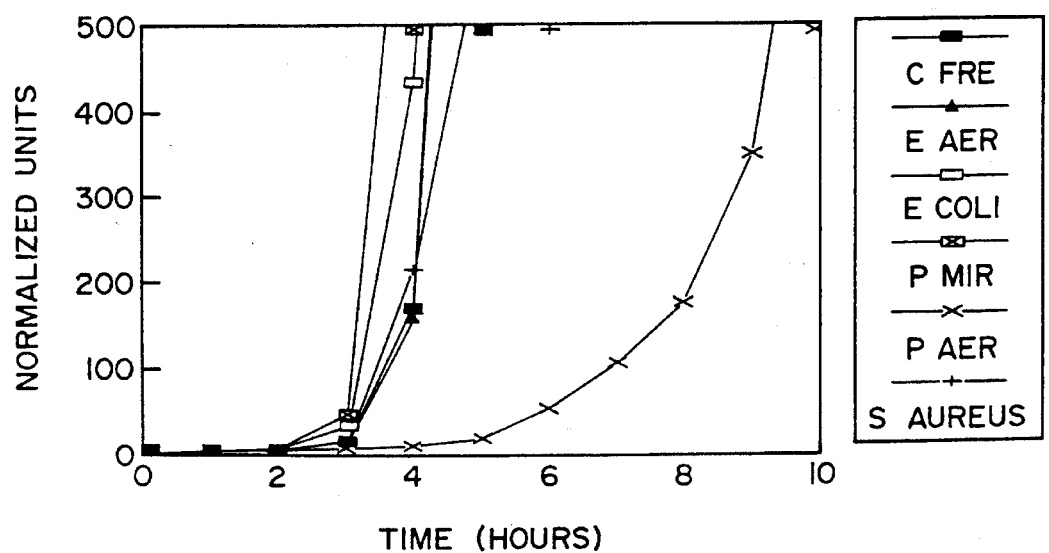
FIG. 32 is a graph that illustrates the fluorescence reading of microorganism growth in a test well in accordance with the method of this invention with different microorganisms.

FIG. 32 shows the data obtained from fluorescence emission reading of growth of a variety of microorganisms and illustrates the general applicability of the method of this invention to rapid growth determination using a fluorescence excitation reading protocol. The graphs show detection of significant quantities of resorufin due to microorganism growth within a four to six hour incubation time period. The design of a particular fluorescence excitation reading protocol and the test and decision algorithms associated therewith involves the collection of data on a number of microorganisms that produce known response and then building the test and decision algorithms such that growth or no growth of unknown organisms can be detected with a high level of confidence. Persons of skill in this art are familiar with the various methods for designing and building such reading protocols and the implementation thereof in connection with this invention involves a straightforward application of known data gathering and protocol generation principles.

The preferred test kit of the present invention employs the resazurin and optionally antibiotic impregnated and dried in a cotton fiber (paper) disk. The disks are rehydrated by adding a small volume, typically 0.1 ml, of the growth media to a well in which the disk has been placed. For microbial testing, the preferred medium is Mueller-Hinton broth as described above. For mammalian cellular testing, the preferred medium is RPMI 1640. The paper disk will be circular, typically having a diameter of 6 mm. The test well will generally be defined by an aperture in a test card, such as those illustrated in FIGS. 19, 21, and 24–27. The useful and preferred concentrations of each of these components in the final reconstituted media are set forth in Table I as follows:

TABLE I

| Component | Useful Concentration Range | Preferred Concentration |
|---|---|---|
| Resazurin | 0.01–0.02 g/l | 0.0015 g/l |
| Methylene Blue | 0.001–0.004 g/l | 0.00025 g/l |
| Potassium Ferricyanide | 0.00005–0.001 M | 0.0001 M |
| Potassium Ferrocyanide | 0.00005–0.001 M | 0.0001 M |

TABLE I-continued

| Component | Useful Concentration Range | Preferred Concentration |
|---|---|---|
| Phosphate Buffer, pH 7.4 | 0.1–0.5 M | 0.25 M |
| Antibiotic | Varying | Varying |

The following examples are offered by way of illustration, not by way of limitation.

EXPERIMENTAL

OVERNIGHT BACTERIAL SUSCEPTIBILITY

Panel Preparation

Antibiotic susceptibility assay panels contain a number of antibiotics each prepared in a 2 fold serial dilution series. The dilution series cover an antibiotic concentration range useful in making both a quantitative determination of the minimum inhibitory concentration (MIC) and a qualitative interpretation of sensitive or resistant for the test organism. Such dilution series are derived from standards published by the National Committee for Clinical Laboratory Standards (NCCLS). A typical dilution series is:

| | micrograms/ml |
|---|---|
| Ampicillin | 0.5 |
| | 1 |
| | 2 |
| | 4 |
| | 8 |
| | 16 |
| | 32 |
| | 64 |

Some dilution series may include intermediate concentrations to satisfy the need for more a precise MIC values.

| | micrograms/ml |
|---|---|
| Gentamicin | 0.5 |
| | 1 |
| | 2 |
| | 4 |
| | 6 |
| | 8 |
| | 16 |
| | 32 |

Antibiotic dilutions were prepared in a stock diluent solution:

| Resazurin | 0.006 g/l |
|---|---|
| Methylene blue | 0.001 g/l |
| Potassium ferricyanide | 0.0004 M |
| Potassium ferrocyanide | 0.0004 M |
| Phosphate buffer, pH 7.4, 0.1 Molar | 1000 ml |

Antibiotic dilutions were prepared in a concentration four times (4×) the strength required in the final assay solution. Diluted antibiotic solutions were each dispensed into a 6 mm diameter paper disk which contained a volume of 25 microliters. Control disks containing the diluent solution and no antibiotic were also prepared. The impregnated disks were air dried or dried in vacuum, and then placed into a plastic disposable tray formed into appropriate receptacles. Each tray then contained the antibiotic dilution series in dried disks and 2 control disks.

Rehydration and Inoculation

Test bacteria were cultured on appropriate bacteriological solid culture medium to produce individual isolated colonies. Several of these colonies were picked from the culture medium and suspended in a tube of sterile saline solution. A suspension of about $10^8$ bacteria/ml was made. This suspension was then further diluted to a concentration of about $10^5$ bacteria/ml using an appropriate growth broth such as Mueller-Hinton broth. A volume of 100 microliters of the inoculated broth was dispensed into each receptacle or the antibiotic test panel containing dried impregnated disks. One control disk was inoculated with bacteria containing growth medium and one control disk was inoculated with sterile growth medium.

Incubation and Reading

The inoculated trays were covered and incubated at 35°–37° C. for 18 to 20 hours. After incubation, the trays were read by visual inspection. If the control well inoculated with bacteria had turned some shade of red, and the control well inoculated with sterile broth had remained blue, the test was used. Each antibiotic dilution series was inspected for color change. Any easily perceptible color change from blue to red indicates bacterial growth and, therefore, resistance to the antibiotic at the concentration contained in that receptacle. The lowest concentration of antibiotic found to produce no color change was identified as the MIC.

A typical antibiotic assay panel will contain 10 to 20 antibiotics. Results for two such panels are provided in the following Tables.

TABLE II

| Antibiotic | Escherichia coli ATCC 29522 | |
|---|---|---|
| | Expected Range (microgram/ml) | Actual Result (microgram/ml) |
| Ampicillin | 2–8 | 2 |
| Ticarcillin | 2–8 | 2 |
| Carbenicillin | 4–16 | 8 |
| Mezlocillin | 2–8 | 2 |
| Piperacillin | 1–4 | 2 |
| Cefazolin | 1–4 | 2 |
| Cefoxitin | 1–4 | 4 |
| Cefuroxime | 2–8 | 4 |
| Cephalothin | 4–16 | 8 |
| Gentamicin | 0.25–1 | 0.5 |
| Tobramycin | 0.25–1 | 0.5 |
| Amikacin | 0.5–4 | 2 |
| Chloramphenicol | 2–8 | 8 |
| Nitrofurantoin | 4–16 | 8 |
| Tetracycline | 1–4 | 2 |

TABLE III

| Antibiotic | Staphylococcus aureus ATCC 29213 | |
|---|---|---|
| | Expected Range (microgram/ml) | Actual Result (microgram/ml) |
| Ampicillin | 0.25–1 | 1 |
| Ciprofloxacin | 0.12–0.5 | 0.25 |
| Norfloxacin | 0.5–2 | 1 |
| Nitrofurantoin | 8–32 | 32 |
| Tetracycline | 0.25–1 | 1 |
| Cefotaxime | 1–4 | 2 |
| Ceftriaxone | 1–8 | 4 |
| Chloramphenicol | 2–8 | 4 |
| Penicillin | 0.25–1 | 1 |
| Vancomycin | 0.5–2 | 1 |
| Oxacillin | 0.12–1 | 0.5 |
| Clindamycin | 0.06–0.25 | 0.12 |

RAPID BACTERIAL SUSCEPTIBILITY

Susceptibility test panels were prepared and inoculated in the identical manner as for overnight susceptibility testing.

Incubation and Reading

Test panels were incubated at 35°–37° C. for a period of time which extended to 18–20 hours. During that time the trays were read periodically, typically hourly using a spectrofluorometer or filter fluorometer adapted for reading the test tray receptacles, and capable of producing light excitation of 540–560 nanometers and detecting fluorescence emission of 580–600 nanometers. The control well containing growth medium with bacteria was monitored until the emission signal indicated detectable growth had been reached. A useful decision algorithm is:

Gcn+1>2×Gcn, detectable growth

Gcn+1<2×Gcn, no detectable growth, where Gcn is the difference between the fluorescence values of the Positive Growth Control (containing bacteria in growth medium) and the Negative Growth Control (containing sterile growth medium) at reading n, and Gcn+1 is at reading n+1.

If this condition was met, then antibiotic containing wells were measured and a similar, but not necessarily identical, algorithm used to determine if an individual well was positive for growth or negative for growth.

Tcn+1>1.5×Tcn, Detectable growth

Tcn+1<1.5×Tcn, no detectable growth, where Tcn is the difference between the fluorescence values of the Test well (containing bacteria, antibiotic, and growth medium) and the Negative Growth Control at reading n, and Tcn+1 is at reading n+1. The well with the lowest concentration of antibiotic failing to meet the Tcn+1>1.5×Tcn is the MIC.

Results of a susceptibility assay are shown in Tables IV and V. Results were calculated using the formulas above and expected results are from NCCLS tables [ ] indicated acceptable range of MIC.

TABLE IV

Organism: *Escherichia coli* ATCC 25922

| Antibiotic | NEG | POS | Antibiotic Concentration (micrograms/ml) | | | | | | | |
| --- | --- | --- | --- | --- | --- | --- | --- | --- | --- | --- |
| | | | 32 | 16 | 8 | 4 | 2 | 1 | 0.5 | 0.25 |
| Cefazolin | | | | | | | | | | |
| Fluor 4 hr | 1468 | 1640 | 1583 | 1514 | 1462 | 1462 | 1487 | 1524 | 1574 | 1612 |
| Fluor 5 hr | 1567 | 2950 | 1694 | 1613 | 1552 | 1557 | 1614 | 1795 | 2166 | 2561 |
| Calc units | — | 3.97 | 1.11 | 1.00 | 0.90 | 0.96 | 1.28 | 2.71 | 5.92 | 9.49 |
| Result | − | + | − | − | − | − | − | + | + | + |
| Expected | − | + | − | − | − | [ − | +/− | +/−] | + | + |
| Chloramphenicol | | | | | | | | | | |
| Fluor 4 hr | 1537 | 1653 | 1751 | 1649 | 1713 | 1744 | 1842 | 1941 | 1988 | 1784 |
| Fluor 5 hr | 1653 | 3803 | 1870 | 1784 | 1865 | 1929 | 2094 | 2308 | 2553 | 3912 |
| Calc units | — | 17.9 | 1.00 | 1.13 | 1.27 | 1.54 | 2.10 | 3.06 | 4.71 | 17.7 |
| Result | − | + | − | − | − | + | + | + | + | + |
| Expected | − | + | − | − | [ − | +/− | +/−] | + | + | + |

TABLE V

Organism: *Staphylococcus aureus* ATCC 29213

| Antibiotic | | | Antibiotic Concentration (micrograms/ml) | | | | | | | |
| --- | --- | --- | --- | --- | --- | --- | --- | --- | --- | --- |
| Oxacillin | NEG | POS | 16 | 8 | 4 | 2 | 1 | 0.5 | 0.25 | 0.12 |
| Fluor 3 hr | 1440 | 1545 | 1625 | 1514 | 1520 | 1500 | 1512 | 1536 | 1573 | 1762 |
| Fluor 4 hr | 1532 | 2686 | 1729 | 1602 | 1602 | 1576 | 1590 | 1609 | 1644 | 1933 |
| Calc units | — | 12.0 | 0.91 | 0.93 | 0.86 | 0.80 | 0.82 | 0.77 | 0.75 | 1.80 |
| Result | − | + | − | − | − | − | − | − | − | + |
| Expected | − | + | − | − | − | − | − | [ − | +/− | +/−] |
| Ciprofloxacin | NEG | POS | 4 | 2 | 1 | 0.5 | 0.25 | 0.12 | 0.06 | 0.03 |
| Fluor 3 hr | 1440 | 1545 | 1502 | 1472 | 1490 | 1494 | 1593 | 1702 | 1798 | 1891 |
| Fluor 4 hr | 1532 | 2686 | 1587 | 1543 | 1568 | 1616 | 1820 | 2135 | 2392 | 2596 |
| Calc units | — | 10.9 | 0.81 | 0.68 | 0.74 | 1.16 | 2.16 | 4.12 | 5.66 | 6.71 |
| Result | − | + | − | − | − | − | + | + | + | + |
| Expected | − | + | − | − | − | [ − | +/− | +/−] | + | + |

MAMMALIAN CELL TOXICITY

This assay may be adapted to testing unknown cell lines (patient cancer cells) against known toxic agents (chemotherapeutic agents) to determine the relative sensitivity or resistance of the cancer cells to treatment with the tested chemotherapeutic agent. Alternatively, the assay may be adapted to testing standard cell lines of known sensitivity to standard toxic agents with agents of unknown toxicity to determine the relative toxicity of the unknown agent. Both assays were performed identically with substitution of cell lines and toxic agents as appropriate.

Assay panels were prepared by inoculating plastic trays containing test receptacles with cultures of test cell lines. Such procedures are known to those skilled in the field. The procedure consisted of growing cells to a standard density, harvesting the cells, and dispensing a known density of cells in tissue culture growth medium into the receptacles. The cells were incubated and allowed to grow for a period of time. Some cell lines attached to the receptacle surface and formed monolayers, others remained in suspension in the growth medium.

When the cells were grown to a preferred density, agents to be tested were added in a series of concentrations, typically in 10 fold dilutions. The cells were then reincubated for a defined period after which the redox indicator was added, the cells reincubated, and the amount of metabolic activity determined by measuring the reduction of the indicator.

Results were reported as the concentration of the test chemical which caused a 50% reduction in cell viability. Using the resazurin fluorescence values, the calculation was made by calculating for each test concentration the % inhibition relative to an untreated control (%UC)

$$\% UC = \frac{\text{fluorescence of test agent dilution}}{\text{Fluorescence of untreated control}} \times 100$$

In a specific example, the sensitivity of cell cultures to doxyrubicin was determined, using stabilized resazurin redox indicator.

Cell lines used:
 P388, ATCC CCL46, Mouse lymphoid neoplasm, suspension culture.
 DU145, ATCC HTB81, Prostate carcinoma, monolayer culture A549, ATCC CCL185, Lung carcinoma, monolayer culture.
 HT1080, ATCC CCL121, Fibrosarcoma, monolayer culture.

Growth Medium:
 RPMI 1640 with Hepes buffer
 10% Fetal bovine serum
 1% Glutamine
 1 unit Penicillin G per ml 0.0025 microgram Amphotericin B per ml Cells were placed into wells of plastic microtiter trays. For each cell line, 16 wells were prepared by placing a suspension of 1250 cells in 100 microliters into each well. Two panels were prepared for each cell line. Panels were incubated for 1 days 35 degrees C., 5% carbon dioxide to establish growth prior to introduction of Doxyrubicin.

Doxyrubicin was prepared in a series of 10-fold dilutions in RPMI growth medium described above. Concentration ranged from 10–4 molar to 10–10 molar. 100 microliters of each dilution was added to individual wells of the cell culture. Panels were then incubated 48 hours.

After incubation, 50 microliters of stabilized resazurin redox indicator was added to each well and the panels reincubated for 4 hours at 37 degrees C. After incubation Panels are read directly on a fluorometer adapted for reading the test tray receptacles, and capable of producing light excitation of 540–560 nanometers and detecting fluorescence emission of 580–600 nanometers. The results are set forth in Table VI.

TABLE VI

| Doxyrubicin Concentration | Cell Line | | | | | | | |
|---|---|---|---|---|---|---|---|---|
| | P388 | | A549 | | HT1080 | | DU145 | |
| | Fluor | % UC | Fluor | % UC | Fluor | % UC | Fluor | % UC |
| Neg Control | 340 | — | 340 | — | 340 | — | 340 | — |
| Pos Control | 2730 | 100 | 7302 | 100 | 6737 | 100 | 3910 | 100 |
| $10^{-3}$ M | 340 | 0 | 344 | 0 | 356 | 0 | 387 | 1 |
| $10^{-4}$ M | 380 | 2 | 1215 | 8 | 390 | 1 | 841 | 14 |
| $10^{-5}$ M | 478 | 6 | 1025 | 15 | 1714 | 22 | 1166 | 23 |
| $10^{-6}$ M | 1625 | 54 | 5156 | 69 | 2526 | 34 | 1421 | 30 |
| $10^{-7}$ M | 2408 | 87 | 6275 | 85 | 4959 | 72 | 3341 | 84 |
| $10^{-8}$ M | 3056 | 114 | 7081 | 97 | 6525 | 97 | 3656 | 93 |
| $10^{-9}$ M | 3094 | 115 | 7719 | 106 | 7421 | 111 | 3942 | 101 |
| $10^{-10}$ M | 2912 | 108 | 8062 | 111 | 7325 | 110 | 3729 | 95 |
| 50% Inhibition | $8 \times 10^{-6}$ M | | $5 \times 10^{-6}$ M | | $3 \times 10^{-6}$ M | | $5 \times 10^{-7}$ M | |

While the methods and apparatus of this invention have been described in accordance with various embodiments, it should be understood that numerous changes and adaptations could be made without departing from the scope of this invention as claimed in the following claims.

What is claimed is:

1. A method for determining susceptibility of cultured cells to growth inhibitory substances, said method comprising:
   culturing the cells in a growth medium in the presence of the growth inhibitory substance;
   exposing the cultured cells to resazurin in the presence of a poising agent in an amount selected to inhibit reduction of the resazurin to resorfurin in the growth medium in the absence of cellular growth, wherein the poising agent comprises a salt selected to maintain the redox potential of the growth medium in the range from about +0.3 volts to +0.45 volts in the absence of cellular growth; and
   observing the reduction of resazurin to resorfurin as an indicator of cellular viability.

2. The method of claim 1 wherein the cells are microorganisms and the growth inhibitory substance is an antibiotic.

3. The method of claim 1, wherein the cells are mammalian tumor cells and the growth inhibitory substance is a cytotoxic drug.

4. The method of claim 1, wherein the salt is selected from the group consisting of potassium ferrocyanide, ferric and ferricinium.

5. The method of claim 1, wherein the poising agent comprises a salt pair present in both its oxidized and reduced forms.

6. The method of claim 5, wherein the salt pair is selected form the group consisting of potassium ferricyanide, potassium ferrocyanide, ferrous/feric, and ferricinium/ferrocene.

7. The method of claim 1, wherein the cultured cells are exposed to the resazurin in the presence of a second poising agent in an amount selected to inhibit reduction of resorfurin to dihydroresorfurin.

8. The method of claim 7, wherein the second poising agent is selected to maintain the redox potential of the growth medium above –0.1 volts.

9. The method of claim 8, wherein the second poising agent is a redox indicator selected from the group consisting of methylene blue, toluidine blue, azure I, and gallocyanine.

10. A cell growth indicator medium comprising an energy source, essential cell nutrients:
    resazurin present in an amount sufficient to be detectable while being substantially non-toxic to cell growth; and
    a poising agent present in an amount selected to inhibit reduction of the resazurin to resorfurin in the growth medium in the absence of cell growth, wherein the poising agent comprises a salt selected to maintain the redox potential of the growth medium in the range from about +0.3 volts to +0.45 volts in the absence of cell growth.

11. The cell growth medium of claim 10, wherein the salt is selected from the group consisting of potassium ferrocyanide, ferric, and ferricinium.

12. The cell growth medium of claim 10, wherein the poising agent comprises a salt pair present in both its oxidized and reduced forms.

13. The cell growth medium of claim 12, wherein the salt pair is selected from the group consisting of potassium ferricyanide-potassium ferrocyanide, ferrous/ferric, and ferricinium/ferrocene.

14. The cell growth medium of claim 13, further comprising a second poising agent in an amount selected to inhibit reduction of resorfurin to dihydroresorfurin.

15. The cell growth medium of claim 14, wherein the second poising agent is selected to maintain the redox potential of the growth medium above –0.1 volts.

16. The cell growth medium of claim 15, wherein the second poising agent is a redox indicator selected from the group consisting of methylene blue, toluidine blue, azure I, and gallocyanine.

17. The cell growth medium of claim 10, present in an absorptive substrate.

18. The cell growth medium of claim 17, lyophilized within the absorptive substrate.

19. A method for determining cytotoxic effect of a test substance on the growth of mammalian cells, said method comprising:

culturing said mammalian cells in a growth medium in the presence of the test substance;

exposing the cultured cells to resazurin, in the presence of a poising agent in an amount selected to inhibit reduction of the resazurin to resorfin in the growth medium in the absence of cell viability, wherein the poising agent comprises a salt selected to maintain a redox potential of the growth medium in the range from about +0.3 volts to +0.45 volts to inhibit reduction of the resazurin to resorfurin in the absence of cell viability; and observing the reduction of resazurin to resorfurin as an indication of cell viability.

20. The method of claim 19, wherein the mammalian cells are neoplastic cells.

21. The method of claim 19, wherein the cells are grown in suspension culture, monolayer culture, or an absorptive disk.

22. The method of claim 19, wherein the culture medium is RPMI 1640.

23. The method of claim 19, wherein the growth medium further includes a second poising agent in an amount selected to maintain a redox potential of the growth medium in the range from about above about −0.1 volts to inhibit reduction of resorfurin to dihydroresorfurin.

* * * * *